(12) United States Patent
Moore

(10) Patent No.: US 10,948,638 B2
(45) Date of Patent: Mar. 16, 2021

(54) SPATIAL AND SPECTRAL FILTERING APERTURES AND OPTICAL IMAGING SYSTEMS INCLUDING THE SAME

(71) Applicant: Stryker European Operations Limited, Carrigtwohill (IE)

(72) Inventor: Frederick Allen Moore, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 14/636,658

(22) Filed: Mar. 3, 2015

(65) Prior Publication Data

US 2015/0309225 A1 Oct. 29, 2015

Related U.S. Application Data

(60) Provisional application No. 61/947,774, filed on Mar. 4, 2014, provisional application No. 62/077,730, filed on Nov. 10, 2014.

(51) Int. Cl.
*G02B 5/22* (2006.01)
*G03B 11/00* (2021.01)
(Continued)

(52) U.S. Cl.
CPC ............ *G02B 5/22* (2013.01); *A61B 1/00186* (2013.01); *G02B 5/005* (2013.01); *G02B 5/201* (2013.01);
(Continued)

(58) Field of Classification Search
CPC ... G02B 5/22; G02B 9/00; G02B 7/20; G02B 3/00; G02B 3/02; G02B 9/08;
(Continued)

(56) References Cited

U.S. PATENT DOCUMENTS 4,693,568 A 9/1987 Takahashi
4,783,152 A 11/1988 Nishimoto
(Continued)

FOREIGN PATENT DOCUMENTS

CH 694 174 A5 8/2004
CN 1230115 C 12/2005
(Continued)

OTHER PUBLICATIONS

US 6,692,429 B1, 02/2004, Imaizumi et al. (withdrawn)
(Continued)

*Primary Examiner* — Stephone B Allen
*Assistant Examiner* — Rahman Abdur
(74) *Attorney, Agent, or Firm* — Morrison & Foerster LLP

(57) ABSTRACT

A filter includes a central filter region, the central filter region to transmit a first wavelength range, a peripheral filter region, the peripheral filter region to block a second wavelength range, and a transition filter region between the central and peripheral filter regions, the transition filter region to transmit or block the second wavelength range differently than the second wavelength range is to be transmitted or blocked in the central and peripheral filter regions. More generally, there may be "N" regions and up to N-1 transition regions.

19 Claims, 14 Drawing Sheets

(51) Int. Cl.
*A61B 1/00* (2006.01)
*G02B 5/00* (2006.01)
*G02B 27/00* (2006.01)
*G02B 5/20* (2006.01)
*G02B 23/24* (2006.01)
*A61B 1/06* (2006.01)
*G02B 27/10* (2006.01)

(52) U.S. Cl.
CPC ..... *G02B 23/2446* (2013.01); *G02B 27/0025* (2013.01); *G02B 27/0068* (2013.01); *G03B 11/00* (2013.01); *A61B 1/0638* (2013.01); *G02B 27/1013* (2013.01)

(58) Field of Classification Search
CPC ........ G02B 13/18; G02B 21/20; G02B 5/005; G02B 27/0025; G02B 5/201; G02B 23/2446; G02B 27/0068; G02B 27/1013; G03B 21/00; G03B 21/14; G03B 11/00; A61B 1/00186; A61B 1/0638
USPC ....... 359/634, 350, 353, 355, 722, 723, 724, 359/739, 740, 784, 785, 789, 790, 792, 359/798, 799, 800, 400, 419, 420, 887, 359/738, 894
See application file for complete search history.

(56) References Cited

U.S. PATENT DOCUMENTS

| | | | |
|---|---|---|---|
| 4,981,342 A | 1/1991 | Fiala | |
| 5,206,759 A | 4/1993 | Ono | |
| 5,212,589 A | 5/1993 | Goodman | |
| 5,276,321 A | 1/1994 | Chang | |
| 5,296,971 A * | 3/1994 | Mori | G02B 9/12 359/716 |
| 5,341,240 A | 8/1994 | Broome | |
| 5,561,525 A | 10/1996 | Toyonaga | |
| 5,684,629 A | 11/1997 | Leiner | |
| 5,790,314 A | 8/1998 | Duck | |
| 5,822,128 A | 10/1998 | Sekine | |
| 5,825,534 A | 10/1998 | Straehle | |
| 5,867,315 A | 2/1999 | Koike | |
| 6,049,422 A | 4/2000 | Ibe | |
| 6,141,159 A | 10/2000 | Nishio | |
| 6,269,057 B1 | 7/2001 | Mcdonald | |
| 6,301,043 B1 | 10/2001 | Lei | |
| 6,665,556 B1 | 12/2003 | Alfano | |
| 6,734,966 B2 | 5/2004 | Mccarthy | |
| 6,747,280 B1 | 6/2004 | Weiss | |
| 6,817,975 B1 | 11/2004 | Farr | |
| 7,057,647 B1 | 6/2006 | Monroe | |
| 7,085,076 B2 | 8/2006 | Sallander | |
| 7,132,654 B2 | 11/2006 | Moisel | |
| 7,180,673 B2 * | 2/2007 | Dowski, Jr. | G02B 5/3083 359/637 |
| 7,230,756 B2 | 6/2007 | Hoogland | |
| 7,315,357 B2 | 1/2008 | Ortyn | |
| 7,466,495 B2 * | 12/2008 | Kuroda | G02B 15/173 359/683 |
| 7,495,833 B2 * | 2/2009 | Powell | G02B 26/10 359/618 |
| 7,518,726 B2 | 4/2009 | Rulison | |
| 7,728,975 B1 | 6/2010 | Totzeck | |
| 7,733,584 B2 | 6/2010 | Kazakevich | |
| 8,619,184 B2 | 12/2013 | Podoleanu | |
| 9,176,069 B2 | 11/2015 | Sullivan et al. | |
| 9,547,178 B2 | 1/2017 | Erdogan | |
| 9,578,252 B2 | 2/2017 | Laroia | |
| 9,648,254 B2 | 5/2017 | Darty | |
| 2002/0080501 A1 * | 6/2002 | Kawae | C09K 11/7774 359/799 |
| 2003/0228053 A1 | 12/2003 | Li et al. | |
| 2004/0186351 A1 | 9/2004 | Imaizumi et al. | |
| 2004/0190762 A1 | 9/2004 | Dowski | |
| 2004/0228005 A1 | 11/2004 | Dowski et al. | |
| 2005/0018312 A1 | 1/2005 | Gruner | |
| 2005/0088730 A1 | 4/2005 | Sangu | |
| 2005/0146634 A1 * | 7/2005 | Silverstein | H04N 5/2254 348/360 |
| 2005/0146720 A1 | 7/2005 | Hansen | |
| 2005/0171079 A1 | 8/2005 | Schrimpf | |
| 2005/0182321 A1 | 8/2005 | Frangioni | |
| 2005/0275956 A1 | 12/2005 | Larson et al. | |
| 2006/0018234 A1 | 1/2006 | Sugi et al. | |
| 2006/0204204 A1 | 9/2006 | Zenzinger | |
| 2006/0221475 A1 | 10/2006 | Liu | |
| 2007/0012704 A1 | 1/2007 | Grinnall | |
| 2007/0035852 A1 * | 2/2007 | Farr | G02B 27/147 359/738 |
| 2007/0081166 A1 | 4/2007 | Brown | |
| 2007/0093993 A1 | 4/2007 | Stork | |
| 2007/0159701 A1 | 7/2007 | Campbell | |
| 2007/0242327 A1 | 10/2007 | Powell et al. | |
| 2008/0049314 A1 * | 2/2008 | Steffen | G02B 6/4298 359/389 |
| 2008/0273247 A1 | 11/2008 | Kazakevich | |
| 2009/0135612 A1 | 5/2009 | Maxik | |
| 2009/0261175 A1 | 10/2009 | Kauppinen et al. | |
| 2009/0290236 A1 | 11/2009 | Wang | |
| 2009/0303317 A1 * | 12/2009 | Tesar | C03C 17/3417 348/65 |
| 2010/0079884 A1 | 4/2010 | Gere | |
| 2010/0262017 A1 | 10/2010 | Frangioni et al. | |
| 2011/0147615 A1 | 6/2011 | Kintz | |
| 2011/0205651 A1 | 8/2011 | Yamano et al. | |
| 2011/0261175 A1 | 10/2011 | Fomitchov | |
| 2011/0316982 A1 * | 12/2011 | Steurer | G03B 11/04 348/49 |
| 2012/0154932 A1 | 6/2012 | Katahira | |
| 2012/0320164 A1 | 12/2012 | Lipton | |
| 2013/0083386 A1 | 4/2013 | Harding | |
| 2013/0194667 A1 | 8/2013 | Inoue | |
| 2013/0253273 A1 | 9/2013 | Duckett, III | |
| 2013/0278747 A1 | 10/2013 | Yang | |
| 2013/0306880 A1 | 11/2013 | Yamano et al. | |
| 2013/0314589 A1 | 11/2013 | Takemoto et al. | |
| 2014/0347646 A1 | 11/2014 | Dmitriev | |
| 2015/0029389 A1 | 1/2015 | Masanori | |
| 2015/0256721 A1 | 9/2015 | Moore | |
| 2015/0260652 A1 | 9/2015 | Verstegen | |
| 2015/0309225 A1 | 10/2015 | Moore | |
| 2016/0291332 A1 | 10/2016 | Moore | |
| 2016/0377782 A1 | 12/2016 | Hague | |

FOREIGN PATENT DOCUMENTS

| | | |
|---|---|---|
| CN | 101238397 A | 8/2008 |
| CN | 101663576 A | 3/2010 |
| CN | 101950041 A | 1/2011 |
| CN | 103033942 A | 4/2013 |
| DE | 2 153 198 A1 | 5/1973 |
| EP | 0646821 A2 | 4/1995 |
| EP | 1 720 050 A1 | 2/2005 |
| EP | 1582894 A1 | 10/2005 |
| EP | 1 607 771 B1 | 12/2005 |
| EP | 1 668 420 B1 | 5/2008 |
| EP | 1777942 A3 | 2/2010 |
| EP | 2 666 402 A1 | 12/2011 |
| GB | 2495198 A | 4/2013 |
| JP | H01284225 A | 11/1989 |
| JP | H 02-119108 A | 5/1990 |
| JP | H075378 A | 1/1995 |
| JP | H08-054515 A | 2/1996 |
| JP | H08-182653 A | 7/1996 |
| JP | H08186830 A | 7/1996 |
| JP | H0943401 A | 2/1997 |
| JP | H09224903 A | 9/1997 |
| JP | H1073762 A | 3/1998 |
| JP | H10115788 A | 5/1998 |
| JP | H10-151104 A | 6/1998 |
| JP | H10276947 A | 10/1998 |

(56) References Cited

FOREIGN PATENT DOCUMENTS

| | | |
|---|---|---|
| JP | H11281887 A | 10/1999 |
| JP | 2001-128927 A | 5/2001 |
| JP | 2002-532748 A | 10/2002 |
| JP | 2002-369223 A | 12/2002 |
| JP | 2003018445 A | 1/2003 |
| JP | 2004047737 A | 2/2003 |
| JP | 2003098570 A | 4/2003 |
| JP | 2003524204 A | 8/2003 |
| JP | 2006165826 A | 6/2006 |
| JP | 2006-285214 A | 10/2006 |
| JP | 2006267391 A | 10/2006 |
| JP | 2007-052441 A | 3/2007 |
| JP | 2007-515768 A | 6/2007 |
| JP | 2008545165 A | 12/2008 |
| JP | 2010160312 A | 7/2010 |
| JP | 2010526342 A | 7/2010 |
| JP | 2011-196873 A | 10/2011 |
| JP | 2013-172967 A | 9/2013 |
| JP | 2015007777 A | 1/2015 |
| KR | 10-2006-0053961 A | 5/2006 |
| WO | 99/19752 A1 | 4/1999 |
| WO | 02/01934 A2 | 1/2002 |
| WO | WO-2007/020561 A1 | 2/2007 |
| WO | WO 2010/111649 A1 | 9/2010 |
| WO | WO 2011/007461 A1 | 1/2011 |
| WO | WO 2011/120688 A1 | 10/2011 |
| WO | WO-2011120688 A1 * | 10/2011 ......... A61B 1/00186 |
| WO | WO 2011120688 A1 * | 10/2011 ......... A61B 1/00186 |
| WO | WO 2012/098806 A1 | 7/2012 |
| WO | 2013/021704 A1 | 2/2013 |
| WO | WO 2013/119992 A1 | 8/2013 |
| WO | 2015/131278 A1 | 9/2015 |
| WO | 2017/035646 A1 | 3/2017 |

OTHER PUBLICATIONS

International Search Report dated Sep. 11, 2015 for PCT/CA2015/050162, Moore.
Extended European Search Report dated Jul. 31, 2017 for corresponding application EP 15758117, Moore.
Canadian Office action dated Jul. 12, 2017 for corresponding application CA 2,941,274, Moore.
Japanese Office Action dated Aug. 25, 2017, for Japanese Application No. 2016-555473.
Korean Office Action dated Sep. 15, 2017 for Korean Application No. 2016-7027305.
Korean Office Action dated Nov. 23, 2018 for Korean Application No. 2016-7027305, filed on Sep. 30, 2016, 13 pages.
Japanese Notice of Allowance dated Jan. 7, 2019, for Japanese Application No. 2016-555473, filed on Sep. 2, 2016, three pages and translation.
European Office Action dated Sep. 18, 2019 for corresponding European Application No. 15 758 117.4.
Japanese Search Report dated Nov. 11, 2019 for corresponding Japanese Application No. 2019-019015.
Korean Notice of Allowance dated Sep. 20, 2019 for corresponding Korean Application No. 10-2016-7027305.
Chinese Office Action dated May 31, 2018 for corresponding Chinese Application No. 201580021609.
Chinese Office Action dated May 7, 2019 for corresponding Chinese Application No. 201580021609.
Korean Office Action dated Jul. 24, 2018 for corresponding Korean Application No. 10-2016-7027305.
Australian Office Action titled Examination Report No. 1 dated Jun. 21, 2018 for Patent Application No. 2016314795, three pages.
Australian Office Action titled Examination Report No. 2 dated Jun. 15, 2019, for Patent Application No. 2016314795, four pages.
Canadian Notice of Allowance dated Aug. 26, 2019, for Patent Application No. 2,981,353, filed on Mar. 29, 2016, one page.
Canadian Notice of Allowance dated Aug. 27, 2019, for Patent Application No. 2,941,274, filed on Mar. 3, 2015, one page.
Canadian Notice of Allowance dated Jan. 25, 2019, for Patent Application No. 3,028,775, filed on Mar. 3, 2015, one page.
Canadian Notice of Allowance dated Jun. 26, 2019, for Patent Application No. 2,941,273, filed on Mar. 3, 2015 one page.
Canadian Office Action dated Jul. 11, 2017, for Patent Application No. 2,941,273, filed on Mar. 3, 2015, three pages.
Canadian Office Action dated Jul. 16, 2018, for Patent Application No. 2,981,353, filed on Mar. 29, 2016, four pages.
Canadian Office Action dated Jun. 21, 2018, for Patent Application No. 2,941,273, filed on Aug. 31, 2016, three pages.
Chinese Notice of Allowance dated Mar. 4, 2020, for Patent Application No. 201580022991.6, filed Mar. 3, 2015, 4 pages (Including English translation).
Chinese Office Action dated Mar. 21, 2019, for Patent Application No. 2016800317428, filed Mar. 29, 2016, twenty-two pages (including English translation).
Chinese Office Action dated Jan. 8, 2019 for Patent Application No. 201580022991.6 filed on Nov. 4, 2016, sixteen pages (including English translation).
Chinese Office Action dated Jun. 22, 2018 for CN Application No. 201580022991.6 filed on Nov. 4, 2016, twenty-four pages (including English translation).
Chinese Office Action dated May 10, 2019 for Patent Application No. 201580022991.6 filed on Nov. 4, 2016, nine pages (including English translation).
Chinese Office Action dated Sep. 26, 2019, for Patent Application No. 201580022991.6 filed on Nov. 4, 2016, ten pages (including English translation).
Chinese Office Action dated Sep. 30, 2019, for Patent Application No. 2016800317428, filed Mar. 29, 2016, twenty-one pages (including English translation).
Chinese Third Office Action dated Feb. 3, 2020, for Patent Application No. 201580021609.X, filed Mar. 3, 2015, 15 pages (including English translation).
European Communication Pursuant to Rules 70(2) and 70a(2) EPC dated Aug. 18, 2017 for EP Application No. 15758117.4, filed on Sep. 5, 2016, one page.
European Office Action dated Jul. 29, 2019, for Patent Application No. 167711407, filed Mar. 29, 2016, five pages.
European Office Action dated Mar. 5, 2020, for Patent Application No. 167711407, filed Mar. 29, 2016, four pages.
European Office Action dated Dec. 20, 2018 for Patent Application No. 15758256.0, filed Mar. 3, 2015, five pages.
European Office Action dated Oct. 11, 2019, for Patent Application No. 15758256.0, filed Mar. 3, 2015, five pages.
European Search Report and Search Opinion dated Aug. 21, 2018, for Patent Application No. 167711407, filed Mar. 29, 2016, eight pages.
European Search Report and Search Opinion dated Mar. 8, 2019, for Patent Application No. 16840465.5, filed Aug. 30, 2016, eight pages.
European Search Report dated Sep. 11, 2017 for Patent Application No. 15758256.0, filed Mar. 3, 2015, ten pages.
Gross. H et al. (ed.) (Jan. 1, 2007). "Handbook of Optical Systems,— Aberration Theory and Correction of Optical Systems," in Handbook of Optical Systems, Aberration Theory And Correction Of Optical Systems, Wiley-VCH, Weinheim, 3:377-379.
Indian Office Action dated May 17, 2019, for Patent Application No. 201617030106, filed Mar. 3, 2015, six pages.
International Preliminary Report on Patentability dated Mar. 15, 2018 for PCT Application No. PCT/CA2016/051023, filed on Aug. 30, 2016, six pages.
International Preliminary Report on Patentability dated Oct. 12, 2017 for PCT Application No. PCT/CA2016/050365, filed on Mar. 29, 2016, seven pages.
International Preliminary Report on Patentability dated Sep. 15, 2016 for PCT/CA2015/050158 filed Mar. 3, 2015, five pages.
International Preliminary Report on Patentability dated Sep. 15, 2016 for PCT/CA2015/050162, filed Mar. 3, 2015, six pages.
International Search Report dated Dec. 13, 2016 for International Application No. PCT/CA2016/051023, filed on Aug. 30, 2016, three pages.

(56) References Cited

OTHER PUBLICATIONS

International Search Report dated May 14, 2015 for PCT Application No. PCT/CA2015/050158 filed Mar. 3, 2015, three pages.
International Search Report dated May 31, 2016, for International Application No. PCT/CA2016/050365, filed on Mar. 29, 2016, four pages.
Japanese Final Office Action dated Jun. 11, 2018, for Patent Application No. 2016-555505, filed on Sep. 2, 2016, eleven pages (including English translation).
Japanese Notice of Allowance dated Jan. 24, 2020, for Japanese Patent Application No. 2018-192776, filed Mar. 3, 2015, seven pages (including English translation).
Japanese Notice of Allowance dated Oct. 4, 2019, for Patent Application No. 2017551311, filed Mar. 29, 2016, seven pages (including English translation).
Japanese Office Action dated Dec. 13, 2019, for Japanese Application No. 2018-510932 filed on Aug. 30, 2016, seven pages (including English translation).
Japanese Office Action dated Jul. 8, 2019, for Japanese Patent Application No. 2018-192776, filed Mar. 3, 2015, nine pages (including English translation).
Japanese Office Action dated Mar. 11, 2019, for Japanese Application No. 2018-510932 filed on Aug. 30, 2016, six pages (including English translation).
Japanese Office Action dated Nov. 9, 2018, for Patent Application No. 2017551311, filed Mar. 29, 2016, eleven pages (including English translation).
Japanese Office Action dated Jul. 14, 2017, for Patent Application No. 2016-555505, filed on Sep. 2, 2016, thirteen pages (including English translation).
Japanese Office Action dated Nov. 25, 2019, for Japanese Application No. 2019-019015, filed Mar. 3, 2015, six pages (including English translation).
Korean Notice of Allowance dated Nov. 12, 2018 for Korean Application No. 2016-7026942 filed on Sep. 28, 2016, three pages (including English translation).
Korean Office Action dated Dec. 13, 2017 for Korean Application No. 2016-7026942 filed on Sep. 28, 2016, twelve pages (including English translation).
Reichman, J. (Jun. 1998). "Handbook of Optical Filters for Fluorescence Microscopy," pp. 2-30, G1-G5, (37 pages) located at: http://www.cyto.purdue.edu/cdroms/micro1/7_spon/chroma/handbk3.pdf, last visited on Jan. 31, 2020.
U.S. Advisory Action dated Nov. 1, 2017, for U.S. Appl. No. 14/636,448, filed Mar. 3, 2015, four pages.
U.S. Final Office Action dated Apr. 4, 2019, for U.S. Appl. No. 15/251,154, filed Aug. 30, 2016, twenty pages.
U.S. Final Office Action dated Aug. 15, 2018, for U.S. Appl. No. 14/636,448, filed Mar. 3, 2015, seven pages.
U.S. Final Office Action dated Aug. 2, 2017, for U.S. Appl. No. 14/636,448, filed Mar. 3, 2015, six pages.
U.S. Non-Final Office Action dated Dec. 14, 2017, for U.S. Appl. No. 14/636,448, filed Mar. 3, 2015, eight pages.
U.S. Non-Final Office Action dated Dec. 2, 2019, for U.S. Appl. No. 15/251,154, filed Aug. 30, 2016, fourteen pages.
U.S. Non-Final Office Action dated Jun. 27, 2017, for U.S. Appl. No. 15/083,357, filed Mar. 29, 2016, thirteen pages.
U.S. Non-Final Office Action dated Nov. 4, 2016, for U.S. Appl. No. 14/636,448, filed Mar. 3, 2015, eight pages.
U.S. Non-Final Office Action dated Sep. 21, 2018, for U.S. Appl. No. 15/251,154, filed Aug. 30, 2016, thirty-one pages.
U.S. Non-Final Office Action dated Sep. 5, 2019, for U.S. Appl. No. 14/636,448, filed Mar. 3, 2015, eleven pages.
U.S. Notice of Allowance dated Feb. 1, 2018, for U.S. Appl. No. 15/083,357, filed Mar. 29, 2016, eight pages.
Written Opinion of the International Searching Authority dated Dec. 13, 2016 for International Application No. PCT/CA2016/051023, filed on Aug. 30, 2016, four pages.
Written Opinion of the International Searching Authority dated May 13, 2015 for PCT/CA2015/050162, filed Mar. 3, 2015, four pages.
Written Opinion of the International Searching Authority dated May 14, 2015 for PCT Application No. PCT/CA2015/050158 filed Mar. 3, 2015, three pages.
Written Opinion of the International Searching Authority dated May 31, 2016, for International Application No. PCT/CA2016/050365, filed on Mar. 29, 2016, five pages.
Australian Examination Report No. 1 dated Mar. 27, 2020, for Patent Application No. 2019204366, filed Aug. 30, 2016, three pages.
Canadian Office Action dated Mar. 13, 2020, for Patent Application No. 3,030,495, filed Mar. 3, 2015, four pages.
Chinese First Office Action dated Mar. 9, 2020, for Patent Application No. 201680063915.4, filed Aug. 30, 2016, twenty-three pages.
Chinese Notice of Allowance dated Mar. 16, 2020, for Patent Application No. 201680031742.8, filed Mar. 3, 2015, seven pages.
Search Report and Written Opinion dated May 20, 2020, directed to BR Application No. BR112018003903-9; 4 pages.
Office Action dated May 1, 2020, directed to CA Application No. 3,030,495; 5 pages.
Office Action dated Apr. 28, 2020, directed to CA Application No. 3,047,435; 4 pages.
Office Action dated Apr. 21, 2020, directed to EP Application No. 16 840 465.5; 7 pages.
Office Action dated Nov. 23, 2018, directed to EP Application No. 15 758 117.4; 4 pages.
Office Action dated Jun. 9, 2020, directed to EP Application No. 15 758 256.0; 5 pages.
Final Rejection dated Jul. 3, 2020, directed to JP Application No. 2018-510932; 6 pages.
Notice of Reasons for Refusal dated May 25, 2020, directed to JP Application No. 2019-019015; 8 pages.
Decision to Grant a Patent dated Jul. 31, 2020, directed to JP Application No. 2019-019015; 6 pages.
European Office Action dated Nov. 23, 2018 for corresponding European Application No. 157581174, 4 pages.
Indian Office Action dated Mar. 27, 2019 for corresponding Indian Application No. 201617030105, 7 pages.

* cited by examiner

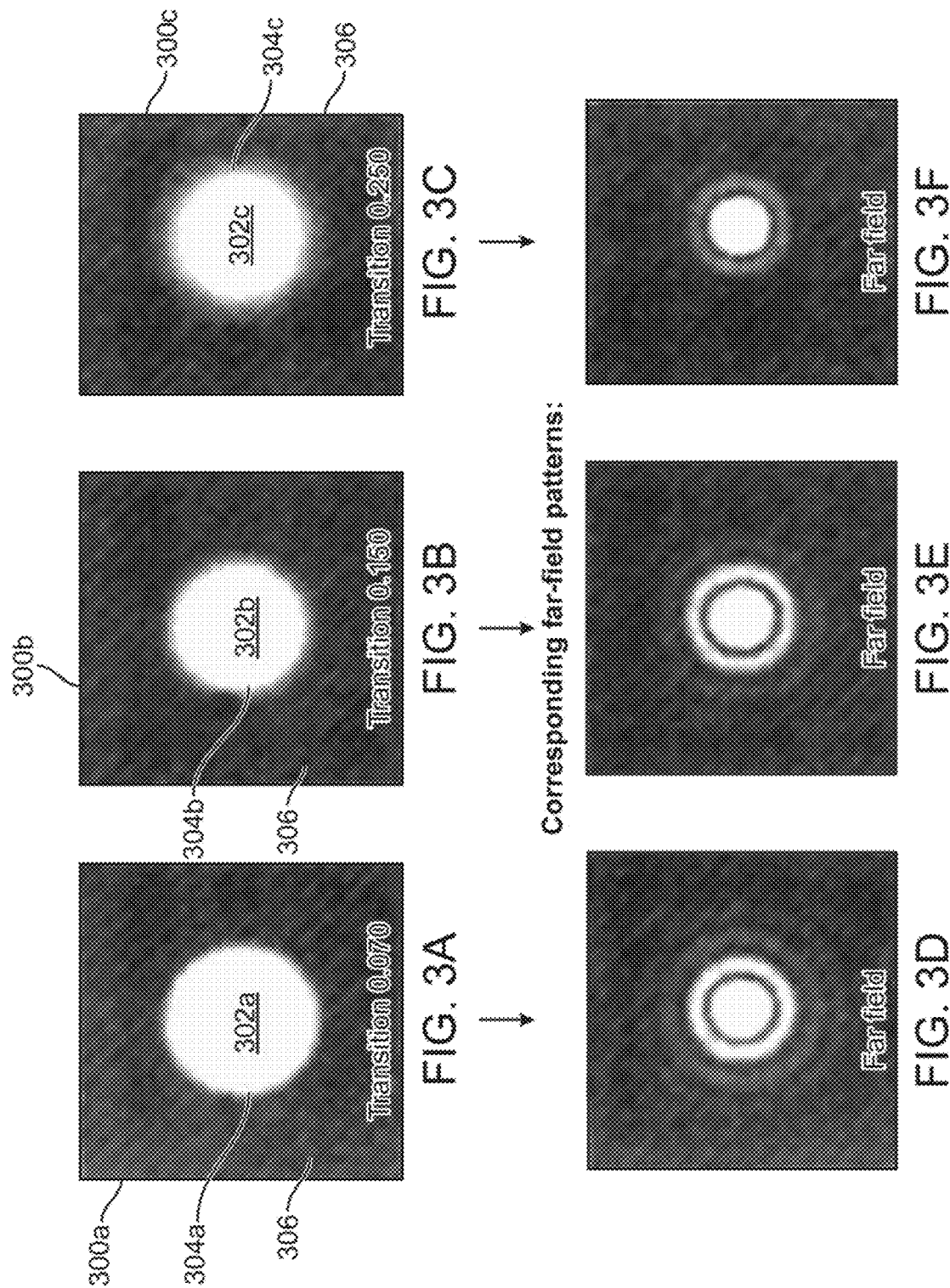

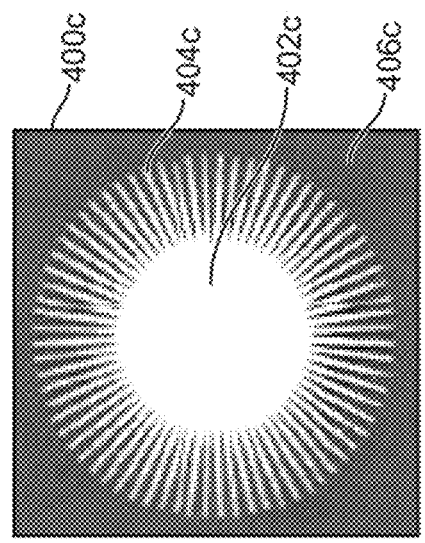
FIG. 4C
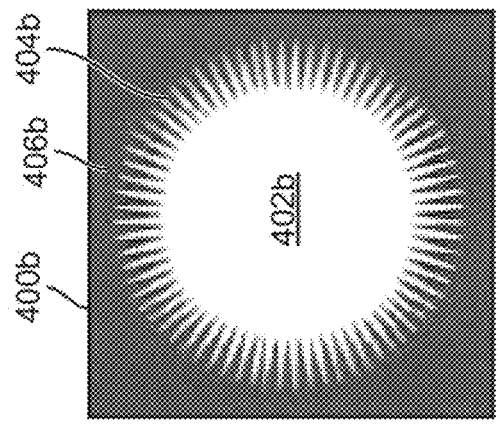
FIG. 4B
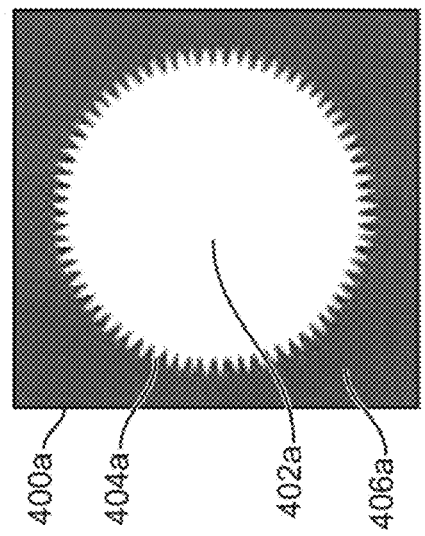
FIG. 4A
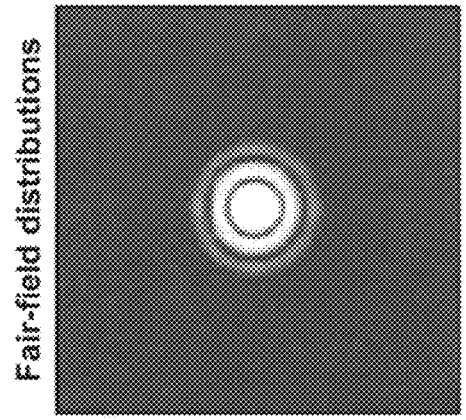
FIG. 4F
Fair-field distributions
FIG. 4E
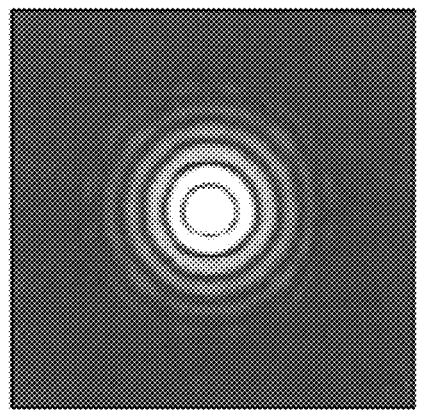
FIG. 4D Apodized apertures Far-field patterns

SPATIAL AND SPECTRAL FILTERING APERTURES AND OPTICAL IMAGING SYSTEMS INCLUDING THE SAME

CROSS-REFERENCE TO RELATED APPLICATION

This application is related to U.S. Provisional Application No. 61/947,774, filed on Mar. 4, 2014, and U.S. Provisional Application 62/077,730, filed on Nov. 10, 2014, the disclosures of which are incorporated herein by reference.

TECHNICAL FIELD

The present disclosure relates generally to the field of imaging. More specifically, the disclosure relates to improving image quality of an optical imaging system.

BACKGROUND

The path taken by a beam of light through an optical system will vary with wavelength. Optical imaging systems exhibit geometric aberrations, such as coma and spherical aberration, differently for different wavelengths. At the image plane, the light rays associated with respective wavelengths not only exhibit variations in aberrations (spherochromatism is a condition wherein spherical aberration varies with wavelength) but also variations in positions. For example, an imaging system, such as a telescope, may form the image of a star such that the blue, green, and red portions of the image exhibit slightly different spot sizes and spot positions. Lateral color (i.e., different magnification for different wavelengths) causes the spot for one wavelength to form at a different position in the image plane relative to the spot centroid of another wavelength. Axial color (i.e., different focal planes for different wavelengths) causes the best image for one wavelength to form at an axial position that is different from that of another wavelength. More generally, all aberrations, such as spherical, astigmatism, coma, field curvature, and distortion, vary with wavelength.

When an image of an object is formed by an imaging device, such as a camera, the influence of the device on the optical information can be described by various means. For example, the image of a point source will be altered according to the device's point spread function (PSF). The PSF characterizes how an imaging system alters the fine details in an object scene when constructing an image scene. An image exhibits aberrations that are brought about by the device and are not otherwise part of the object. More generally, the image field resolution and contrast will be determined by an imaging device's modulation transfer function (MTF). Both the PSF and the MTF will exhibit wavelength dependencies, system aperture geometry dependencies, and aberration dependencies; i.e., MTF will be different for different wavelengths and different for different aperture geometries and will depend also on the extent to which the final wavefront is diffraction limited or aberration-limited.

The PSF, the MTF, and other such characterizations of real imaging systems, account for and include diffraction effects and aberration effects. For example, if an aberration is introduced in an imaging system, both the MTF and the PSF will change, decreasing image quality. A system that is aberration limited across the whole field of view will show improved performance when the aperture is reduced. In such a system, however, it may occur that one wavelength is predominantly responsible for the off-axis performance deterioration.

Some imaging systems exhibit more aberrations off-axis than on-axis and will exploit vignetting as a means to control off-axis aberrations that would otherwise adversely affect image quality. Vignetting involves selectively stopping peripheral rays from reaching the image plane. For example, coma can be reduced by preventing some rays associated with off-axis field positions from reaching the image plane. These rays can be blocked in regions, before and/or after the system aperture stop. The rays may be blocked by insertion of a limiting (vignetting) aperture or by under-sizing a lens that is not located at the system aperture stop. However, in systems that image more than one wavelength where different wavelengths have different intensities, such vignetting may reduce too much light at a low intensity wavelength, so that an image for the low intensity wavelength may not be discernible.

SUMMARY

One or more embodiments are directed to a filter including a central filter region, the central filter region to transmit a first wavelength range, a peripheral filter region, the peripheral filter region to block a second wavelength range, and a transition filter region between the central and peripheral filter regions, the transition filter region to transmit or block the second wavelength range differently than the second wavelength range is to be transmitted or blocked in the central and peripheral filter regions.

The central filter region may block the second wavelength range and the transition filter region is to transmit the second wavelength range.

The central filter region may transmit the second wavelength range and the transition filter region may transmit more of the second wavelength range than the peripheral filter region and less of the second wavelength range than the central filter region.

The transition filter region may gradually change transmission of the second wavelength range from the central filter region to the peripheral filter region.

The transition filter region may include first portions that are to block the second wavelength range between second portions that are to transmit the second wavelength range.

The transition filter region may gradually increase blocking of the second wavelength range from the central filter region to the peripheral filter region.

The first portions of the transition filter region may be of a same material as the peripheral filter region.

The transition filter region may transmit the first wavelength range.

The filter may substantially equalize point spread functions of the first and second wavelength ranges.

The first and second wavelength ranges may partially overlap.

The first and second wavelength ranges may not overlap.

One or more embodiments are directed to a system for use with more than one wavelength range, the system including a first wavelength dependent filter adjacent a first conjugate of a system aperture, and a second wavelength dependent filter at a second conjugate of the system aperture, wherein the first and second wavelength dependent filters substantially equalize point spread functions of the more than one wavelength ranges.

One or more embodiments are directed to a system aperture and an optical system to image an object onto an image plane, the filter system being between the system aperture and the image plane, the filter system including a filter having a first filter region in a center of the filter, the first filter region to transmit first and second wavelength ranges, a second filter region to transmit the first wavelength range and block the second wavelength range, and an adjuster to alter an effective size of the first filter region in the filter system.

The adjuster may translate the filter in axial space relative to the image plane.

The second filter region may include multiple filter portions positioned around the optical axis and the adjuster may translate the multiple portions in radial space.

The filter may include a substrate having multiple first filter regions therein and the adjuster may translate the substrate in radial space.

The adjuster may rotate the filter.

One or more embodiments are directed to a method of filtering at least a first wavelength range and a second wavelength range, the method including transmitting a central portion of the first wavelength range, blocking a peripheral portion of the second wavelength range, and transmitting or blocking a transition portion of the second wavelength range between a central portion and the peripheral portion differently than the second wavelength range is transmitted or blocked in the central portion and the peripheral portion.

The method may include blocking the central portion of the second wavelength range, wherein transmitting the second wavelength range in the transition portion.

The method may include transmitting the central portion of the second wavelength range, wherein the transition portion transmits more of the second wavelength range than for the peripheral portion and less of the second wavelength range than the central portion.

One or more embodiments is directed to a kit including a filter and a beam splitter to split the first and second wavelength ranges.

The kit may include a plurality of relays.

The kit may include an objective lens.

One or more embodiments are directed to an endoscope including a filter.

The filter may or may not be positioned at or near a system aperture or conjugate thereof of the endoscope.

BRIEF DESCRIPTION OF THE DRAWINGS

Features will become apparent to those of skill in the art by describing in detail exemplary embodiments with reference to the attached drawings in which:

FIGS. 3A to 3F illustrate schematic view of exemplary wavelength dependent aperture filters according to embodiments.

FIGS. 4A to 4F illustrate schematic view of exemplary wavelength dependent aperture filters according to embodiments.

DETAILED DESCRIPTION

Figure 1:
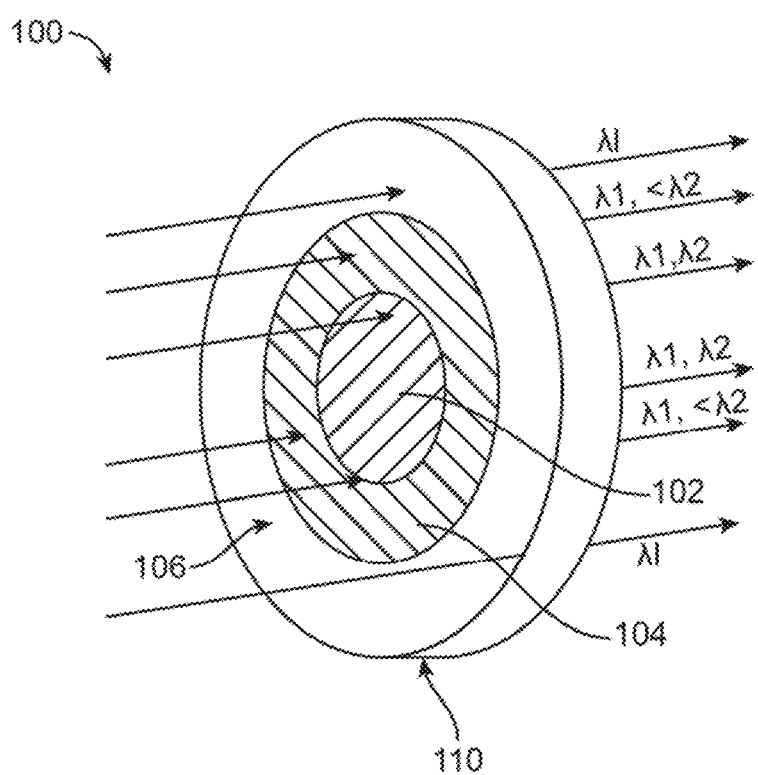
FIG. 1 illustrates a schematic view of an exemplary wavelength dependent aperture filter according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Generally, corresponding or similar reference numbers will be used, when possible, throughout the drawings to refer to the same or corresponding parts.

An optical system designed for the human eye may be optimized for the visible spectrum, with particular weight given to the middle, or green, part of the spectrum. However, imaging systems, in which an electronic image sensor is located in an image plane, may operate over a much larger spectral region that may include visible, ultraviolet, near infrared regions, and so forth. The design of an imaging system becomes more complex as its operating bandwidth increases.

In particular, imaging systems that operate over bandwidths having different sources, e.g. directly from an illumination source, reflected from or transmitted by an object, direct observation, and so forth, may have illumination intensities that vary widely for different wavelength ranges. For example, a wavelength range having a relatively large intensity may benefit from some beam correction to improve an image, but a wavelength range having a relatively low intensity may not be able to afford loss of light. When the imaging system includes at least a partial common optical path and in which magnifications are to be maintained across the wavelength regions, these tradeoffs are amplified.

Therefore, in accordance with embodiments, by recognizing that, in optical imaging systems (a) vignetting is used to reduce aberrations at the image plane and (b) aberrations at the image plane may exhibit detectable wavelength dependencies, vignetting and/or obscuration may be applied differently to different wavelengths in order to improve image acuity of a wavelength range a relatively high intensity, while leaving another wavelength range having a relatively low intensity unaffected. This may be particularly useful in optical imaging systems that operate at high speeds (low f-numbers, such as f/2) and/or operate with wide angular fields of view. In such systems, off-axis aberrations are difficult to correct.

If a system does not exhibit aberrations, or the aberrations are not discernible, then its performance is said to be "diffraction limited." In such instances, both the PSF and the MTF are determined entirely by diffraction effects. Diffraction effects are determined by the shape, size, and structure of the system aperture. In some devices, such as a camera, there may be a single system aperture called a stop or f-stop. In other devices, such as an endoscope with relays, conjugate planes may occur, resulting in more than one location that can operate as a system aperture.

Diffraction-limited performance improves with decreasing f-number. This means that for a specific focal length, a large diffraction-limited aperture will produce better image quality than a small diffraction-limited aperture. The shape and structure of diffraction patterns are directly linked to the size and structure of the system aperture, and to the wavelength of the beam passing through the aperture.

Diffraction-limited performance varies with wavelength. A given aperture will exhibit higher performance at shorter wavelengths. For example, if a first wavelength, e.g., red at 650 nm, is 1.4 times longer than a second wavelength, e.g., blue at 460 nm, then size of the diffraction-limited point spread function for the longer wavelength will be 1.4 times larger than the size of the diffraction-limited point spread function for the shorter wavelength.

In a diffraction limited imaging system, diffraction limited performance at some or all of the wavelengths may be adjusted in order to improve overall image quality. For example, an apodized wavelength dependent aperture located at or near the system aperture (or conjugate thereof) may serve to change the size and alter the structure of the diffraction pattern associated with one wavelength in order that the width of its intensity profile at the image plane will be more closely matched to that of another wavelength.

Image quality in real systems is determined not only by the transfer characteristics of the optics, but also by the sampling characteristics of the sensor at the image plane.

In a diffraction limited imaging system, diffraction limited performance at some or all of the wavelengths may be adjusted in order to more closely match the sensor's spatial sampling characteristics. For example, if a sensor samples one wavelength at a higher spatial frequency than another, a PSF for a more-frequently sampled wavelength could be of a smaller form than that for the less-frequently sampled wavelength.

One or more embodiments are directed to using a wavelength dependent aperture filter positioned at the system aperture, or any conjugate plane of the system aperture as may occur in the relay lenses of an endoscope, or in the f-stop plane (system aperture location) of an imaging system, to alter the diffraction pattern (or point spread function) for the optical system for at least one wavelength range, i.e., a subset of wavelengths to be imaged.

One or more embodiments are directed to using variable geometry wavelength dependent vignetting that involves stopping or blocking a portion of the rays that will arrive at an off-axis image position for a subset of wavelengths passing through the vignette aperture and with some control over both (a) the image plane location of the transition from unvignetted to vignetted and (b) the width of the transition region on the image plane from unvignetted to vignetted optics.

One or more embodiments are directed to stopping a portion of the beam for a subset of wavelengths using an aperture that is or is not located at the system aperture or conjugate thereof.

One or more embodiments are directed to a soft or gradient apodized wavelength dependent aperture that may be positioned at a plane that is or is not conjugate to the system aperture, enabling selective stopping of one or more wavelength ranges at one or more field positions.

Use of any of the wavelength dependent filters discussed below at or near a system aperture or conjugate thereof will alter the wavelength dependent diffraction limited or aberration limited performance for the wavelengths affected by the filters, e.g., diffraction and aberrations may be controlled for the whole field, i.e., for both on-axis and off-axis image positions. Use of any of the wavelength dependent filters discussed below not at a system aperture or conjugate thereof will alter the wavelength dependent aberration limited performance for the wavelengths affected by the filters, e.g., diffraction and aberrations may be controlled for off-axis image positions.

Details of the above various embodiments will be described in detail below. While a general outline of regions of the wavelength dependent filter apertures may be illustrated below as being round, these regions may be square, oval, rectilinear, or take any other shape. Additionally, the different regions may have different shapes and/or some regions may be discontinuous. Further, figures showing various embodiments, the figures are intended as representative and not exact. Thus, the figures do not represent exact proportions of, or distances between, constituent elements. Finally, the description of applications using the wavelength dependent aperture filter have been simplified for clarity by eliminating additional elements or specifics of particular elements that would not aid in further understanding of embodiments, and would be understood by those of skill in the art.

Wavelength Dependent Aperture Filters Having Transition Regions

FIG. 1 illustrates general characteristics a wavelength dependent aperture filter 100, which can be incorporated into an imaging device, e.g., an endoscope, a borescope, a camera, and so forth. The wavelength dependent aperture filter 100 may be formed on the main lens of an imaging device or may be formed on a removable substrate 110, i.e., may be released from and secured to, relative to the imaging device.

As shown in FIG. 1, the wavelength dependent aperture filter 100 includes a first or central region 102, a second or transition region 104 encircling (and typically abutting) the first region 102, and a third or peripheral region 106 (and typically abutting) surrounding the second region 104. The second region 104 may serve as a transition region between the first and third regions 102, 106. For example, the first region 102 may pass all of a first wavelength range and a second wavelength range, the third region 106 may pass all of the first wavelength range and block all of the second wavelength range, and the second region 104 may treat the second wavelength range differently than the first and third regions 102, 106.

Different regions of the wavelength dependent aperture filter 100 have different light transmission properties, as described in more detail below. The shading shown in FIG. 1 and other figures is provided only to enhance visual perception of the various elements, and is not intended to represent any requirement, coloring, or physical property of the embodiment or any portion thereof. Likewise, although a general outline of the regions is illustrated as being round in FIG. 1, these regions may be square, oval, rectilinear, or take any other shape. Additionally, the different regions may have different shapes (See, e.g., FIG. 4A to 4C, 6A to 6C) and/or some regions may be discontinuous (See, e.g., FIG. 2) Similarly, for FIG. 1 and other figures showing various embodiments, the figures are intended as representative and not exact. Thus, the figures do not represent exact proportions of, or distances between, constituent elements.

For example, the first region 102 of the wavelength dependent aperture filter 100 may be uncoated, i.e., may allow all light to pass. The second region 104 may be selectively coated with a wavelength selective coating, e.g., a dichroic or thin film coating, e.g., the wavelength selective coating may form a pattern in the second region 104 (See, e.g., FIGS. 2, 4A-4C, and 5). The third region 106 may be coated with a wavelength selective coating, e.g., may be fully coated with the wavelength selective coating used in the second region 104. The wavelength selective coating may form a band-pass filter for the transmission of light of a particular wavelength range, while substantially or completely blocking light of another wavelength range. For example, the wavelength selective coating may form a band-pass filter for a second wavelength range, such that a pattern of the wavelength selective coating the second region 104 forms a transition region between the first region 102, in which all light of the second wavelength range is passed, and the third region 106, in which all light of the second wavelength range is blocked. All three regions 102 to 106 may transmit light of the first wavelength range, e.g., the wavelength dependent aperture filter 100 may appear transparent to the first wavelength range such that the first wavelength range is not stopped down. The first and second wavelength ranges may partially overlap.

Thus, an imaging system may benefit from a thin film aperture because strong signals, e.g., the wavelengths in the second wavelength range, may be blocked at the periphery, while other weaker signals, e.g., wavelengths in the first wavelength range, are not blocked.

Therefore, the wavelength dependent filter aperture 100 may provide improvements in an imaging device where some wavelength ranges have a strong intensity and other wavelength ranges have a weak intensity. In a particular example of fluorescence imaging, visible light has a strong intensity and fluorescence has weak intensity.

While the wavelength dependent aperture filter 100 has been illustrated as being on a single surface of a single substrate, the wavelength dependent aperture filter 100 may be realized on opposing surfaces of a single substrate, spread over multiple substrates, and so forth.

In some aspects, the second region 104 may include a wavelength dependent apodization configuration to further differentiate the optical system's PSF and MTF for the second wavelength range. Effects of apodization are achievable through apodization of an aperture's boundary. For example, the second region 104 between the first and third regions 102 and 106 of FIG. 1 may include a patterned region of a first wavelength dependent filter used in the first region 102 (if any) and a second wavelength dependent filter used in the third region 106, as discussed in detail below with reference to FIG. 2.

Figure 2:
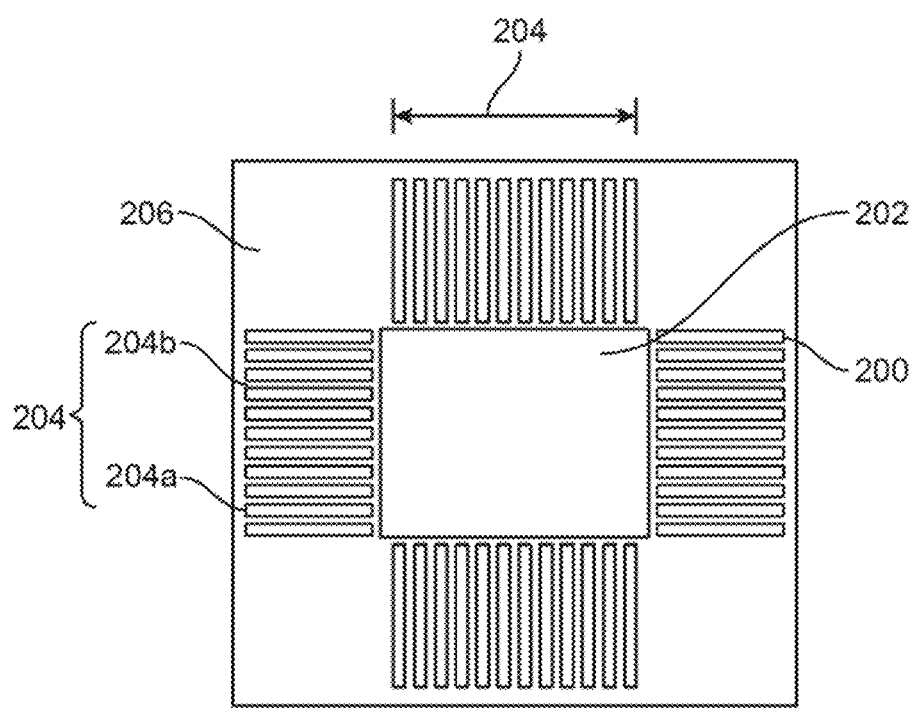
FIG. 2 illustrates a schematic view of an exemplary wavelength dependent aperture filter according to an embodiment.

FIG. 2 illustrates a specific example of a wavelength dependent aperture filter 200 in accordance with an embodiment. The wavelength dependent aperture filter 200 includes a first region or central 202, a second or transition region 204, and a third or peripheral region 206.

The transition region 204 may include a first portion 204a and a second portion 204b. The first portion 204a may include a first wavelength dependent filter (if any) used in the first region 202, such that the first and second wavelength ranges are passed. The second portion 204b includes a wavelength dependent filter, e.g., a second wavelength dependent filter used in the third region 206, such that only the first wavelength range is passed.

In this particular embodiment, the wavelength dependent aperture filter 200 is has a geometry compatible with a typical sensor's pixel geometry, e.g., is based on a quadrangle rather than a circle shown in FIG. 1. Due to this geometry, the second or transition region 204 may be discontinuous, e.g., may extend only parallel to sides of the quadrangle, with the third region 206 filling the remainder of the wavelength dependent aperture filter 200 outside the first region 202.

FIGS. 3A to 3C illustrate specific examples of wavelength dependent aperture filters 300a to 300c in accordance with embodiments. The wavelength dependent aperture filters 300a to 300c include first or central regions 302a to 302c, second or transition regions 304a to 304c, and a third or peripheral region 306, respectively. Here, the wavelength dependent aperture filters 300a to 300c are based on a circular geometry.

In this particular embodiment, the second regions 304a to 304c have a soft or gradient transition, i.e., rather than a binary type pattern of FIG. 2, in which the second wavelength range is blocked or passed, the second regions 304a to 304c gradually decrease the amount of the second wavelength range that is blocked from the no blockage of the first region 302 to the complete blockage of the third region 306. When used at the system aperture (or conjugate thereof) this embodiment can be used to reduce the portion of light that is diffracted out of the central core. The effect that increasing the size of the transition region 304a to 304c relative to the diameter of the first regions 302a to 302c (e.g., 0.07, 0.15, 0.25, respectively, in FIGS. 3A-3C) has on the far field images for the second wavelength range is shown in corresponding FIGS. 3D-3F.

FIGS. 4A to 4C illustrate wavelength dependent aperture filters 400a to 400c, respectively, in accordance with embodiments. The wavelength dependent aperture filters 400a to 400c may include first regions 402a to 404c, second regions 404a to 404c, and third regions 406a to 406c, respectively. Here, the wavelength dependent aperture filters 400a to 400c are based on a circular geometry.

As shown in FIGS. 4A-4C, the second regions 404a to 404c between the first regions 402a to 402c and the third regions 406a to 406c may include a serrated edge transition configured to alter the diffraction pattern in the far field, when the apodized aperture is positioned at or near to the system aperture or if it is positioned at or near to a plane that is conjugate to the system aperture. The effect that increasing the size of the serrations of the second region 404a to 404c in FIGS. 4A-4C has on the far field images for the second wavelength range is shown in corresponding FIGS. 4D-4F. Each of the V-shaped serrations may be replaced by a series of steps approaching one another from opposite directions and eventually meeting one another at the border of the third regions 406a to 406c.

Figure 5:
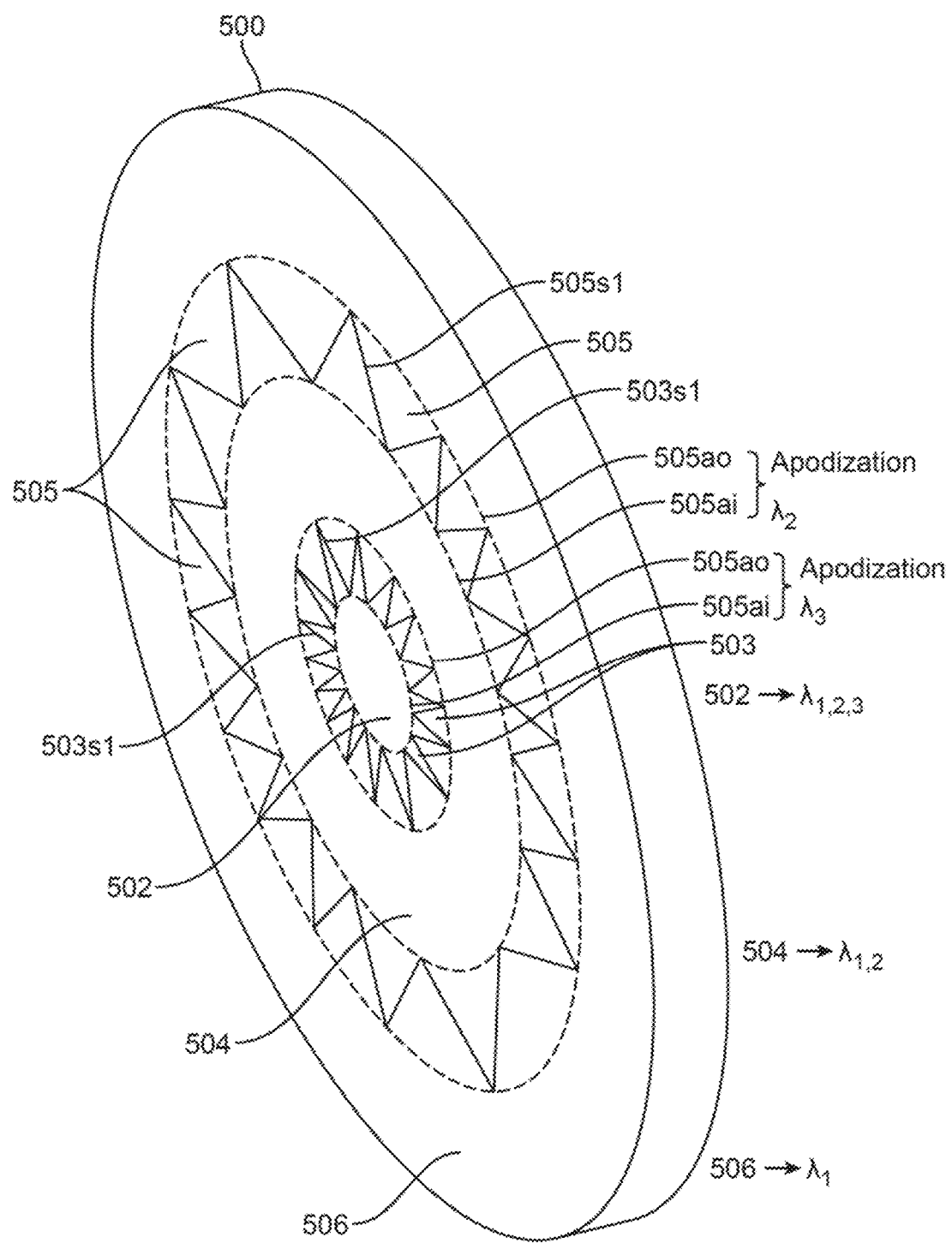
FIG. 5 illustrates a schematic view of an exemplary wavelength dependent aperture filter according to an embodiment.

FIG. 5 illustrates a wavelength dependent aperture filter 500 for use with three wavelength ranges. The wavelength dependent aperture filter 500 may include a first or central region 502, a second region 504, and a third or peripheral region 506. The wavelength dependent aperture filter 500 has two transition regions: transition region 503, which transistions between 502 and 504; and transition region 505, which transitions between 504 and 506. The dashed lines 503ai, 503ao, 505ai, 505ao in FIG. 5 are for indicating the general circular geometry of the wavelength dependent aperture filters 500. The dashed lines 503ai and 503ao are for indicating the radial boundaries for the transition regions 503. The dashed lines 505ai and 505ao are for indicating the radial boundaries for the transition region 505. The dashed lines are not physically part of the wavelength dependent aperture filter 500. In contrast to FIG. 2, in which the pattern of the of the portions 204a and 204b in the transition region 204 is the same within the transition region 204, the serrated portions in FIG. 5 gradually alter the amount of light being transmitted. The features 204, 503, and 505 all change the diffraction pattern for a a wavelength region that is passed on one side of the region and stopped on the other side.

Again, the first region 502 may be uncoated, i.e., may allow all light to pass. The second region 504 may allow the first and second wavelength regions to pass, while blocking the third wavelength region. The third region 506 may only allow the first wavelength region to pass, while blocking the second and third wavelength regions. The second region 504, is bound by two annular transition (or apodization) regions 503 and 505. The inner transition region 503, bounded within 503ai and 503ao, imposes an apodization function on the third wavelength region for which the diffractive pattern is affected by the geometry of the feature 503s1 in the region 503, bounded by 503ai and 503ao. Inside the boundary 503s1, all wavelengths pass. Outside the boundary 503s1, the third wavelength region is blocked. The amount of light for the third wavelength region passed within region 503 gradually decreases from 503ai to 503ao and the diffraction pattern for the third wavelength region is altered by the geometry of the boundary 503s1. Only the third wavelength region is affected by the features within the inner transition region 503. The outer transition region 505, bounded within 505ai and 505ao, imposes an apodization function on the second wavelength region for which the diffraction pattern is affected by the geometry of the feature 505s1 in the region 505, bounded by 505ai and 505ao. Inside the boundary 505s1, both the first and the second wavelength regions pass. Outside the boundary 505s1, the second wavelength region is blocked. The amount of light for the second wavelength region passed within the region 504 gradually decreases from 505ai to 505ao and the diffraction pattern for the second wavelength region is altered by the geometry of the boundary 505s1. Only the second wavelength region is affected by the features within the region 505.

In the case shown in FIG. 5, the third wavelength range has a far field diffraction pattern in accordance with boundary 503s1, the second wavelength range has a far field diffraction pattern in accordance with boundary 505s1, and the first wavelength range has a far field diffraction pattern in accordance with the limit and shape of the disk itself.

For example, in an aberration-limited system, if positioned at or near the optical system's aperture stop or conjugate thereof, an apodization configuration occurring at an aperture boundary, such as at second region 504 in FIG. 5, may provide enhanced resolution of an image formed from light passing through either the circular segment (if its pass through light is stopped by the annular region) or the annular region (if its pass through light is stopped by the circular region) without affecting the luminous intensity of the unstopped light passing through both the circular and the annular segments.

According to various aspects, fabrication of the transition regions may be achieved using masked coating technology. "Masked coating" refers to the process where in a mask is used in order to prevent a region of a subject's surface from being coated during the coating process. The mask does not remain on the substrate of the final product. Masked coatings include dichroic form.

Central Obscuration Wavelength Dependent Aperture Filters

Figure 6A:
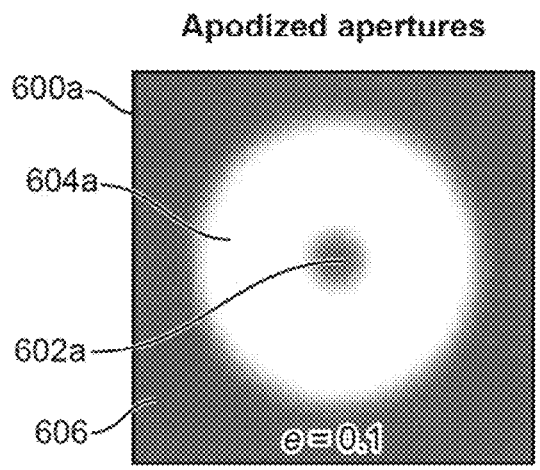
FIGS. 6A to 6F illustrate exemplary obscuration configurations according to embodiments.
Figure 6B:
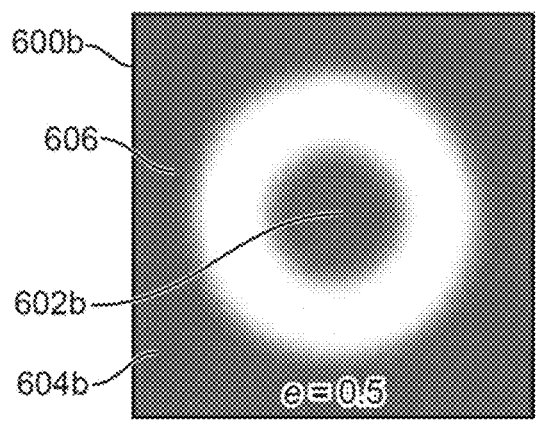
Figure 6C:
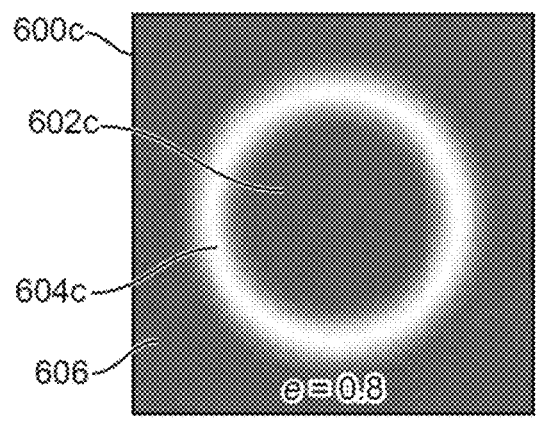
Figure 6D:
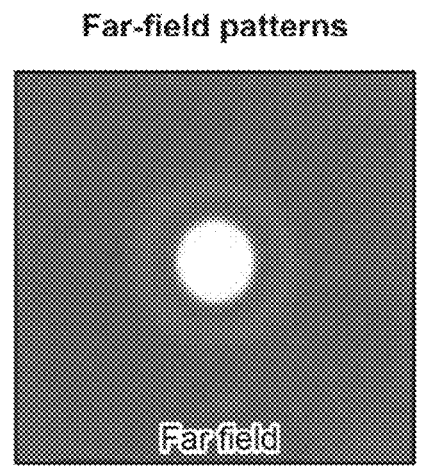
Figure 6E:
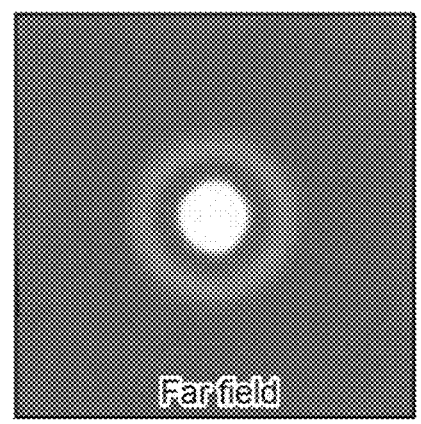
Figure 6F:
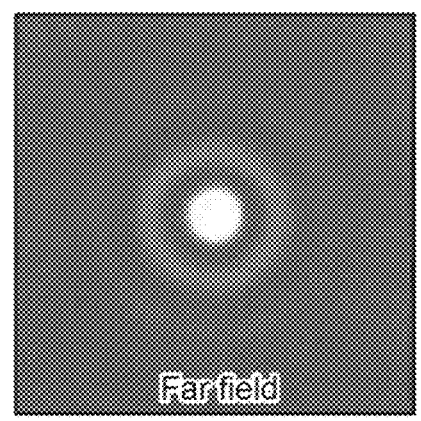

FIGS. 6A to 6C illustrate wavelength dependent aperture filters 600a to 600c, respectively, in accordance with embodiments. Each of the wavelength dependent aperture filters 600a to 600c may include first regions 602a to 602c, second regions 604a to 604c, and a third region 606, respectively. Here, the wavelength dependent aperture filters 600a to 600c are based on a circular geometry.

In FIGS. 6A to 6C, rather than passing all of the light, the first regions 602a to 602c block the second wavelength range while passing the first wavelength range. The second regions 604a to 604c pass both the first and second wavelength ranges, e.g., may be uncoated, and the third region 606 may block the second wavelength range while passing the first wavelength range, e.g., may have the same filter as the first regions 602a to 602c. Thus, the first regions 602a to 602c in FIGS. 6A to 6C serve as central obscurations for the second wavelength range. The obscurations may be in place of or in addition to the transition regions noted above, where such transitions regions would now be between the second regions 604a to 604c and the third region 606 and also between 604a to 604c and 602a to 602c.

In such instance where a lower intensity long wavelength, for example NIR fluorescence, and a higher intensity short wavelength, for example blue light, are imaged through a single system, the aperture configuration of FIGS. 6A through 6C may serve to pass all of the fluorescence light unobscured (this being the "first" wavelength" range) and may further pass the the brighter shorter wavelength though the obscured portion of the aperture (this being the "second" wavelength range). The size of annular pass through zone for the blue light may be used to equalize the point spread function to be similar to that of the NIR light, without reducing the throughput of the weaker NIR light.

Variable Geometry Wavelength Dependent Aperture Filters

Another approach to treating one wavelength range different from another involves variable geometry wavelength dependent filtering. This may be done at a system aperture if it is desirable to achieve wavelength-dependent point spread function control across the field. Alternatively, it may also be done away from the system aperture (or conjugate thereof) if it is desirable to achieve wavelength-dependent vignetting, in which a portion of the rays that will arrive at an off-axis image position are blocked or stopped, and doing this only for a subset of wavelengths passing through the vignette aperture. It may be appreciated that a variable geometry, wavelength-dependent system aperture requires similar technology implementation to that of variable geometry, wavelength-dependent vignetting, except that it will be simpler: the system aperture occurs in one conjugate plane and its variable components will operate within this plane, whereas the vignetting aperture will also need to be movable to other planes. For these reasons, the discussion will explore that more complex of the two: the variable geometry, wavelength-dependent vignetting aperture. In accordance with an embodiment, this may be realized by controlling both (a) the location of the transition from unvignetted to vignetted as it appears on the image plane and (b) the width of the transition region from unvignetted to vignette as it appears on the image plane. Vignetting may be implemented at any location that is not located at a pupil (or f-stop), or conjugate thereof, or at an image plane or conjugate thereof.

Figure 7:
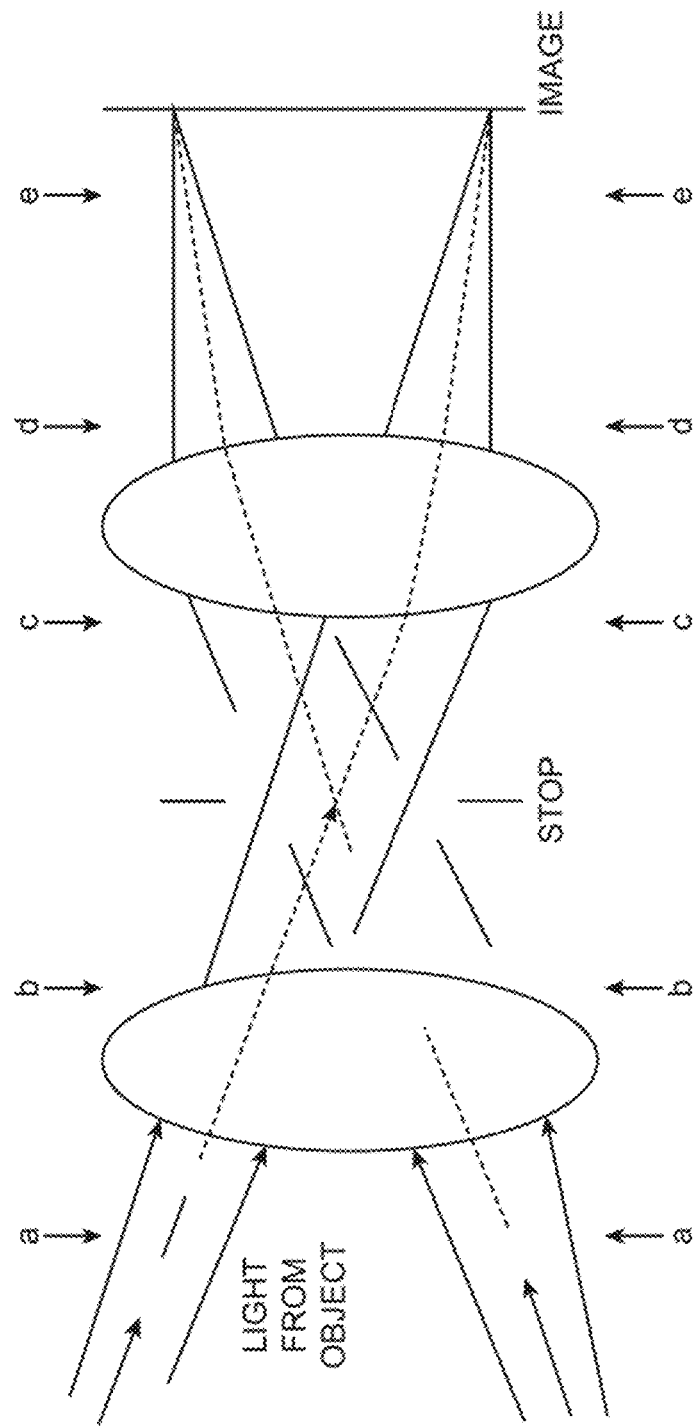
FIG. 7 illustrates a schematic view of axial locations for variable geometry vignetting in an imaging system.

FIG. 7 illustrates axial locations for variable geometry wavelength dependent vignetting in an imaging system generally. As may be seen therein, vignetting may be introduced at locations a through e, but not at the pupil plane or the image plane or conjugates thereof, where the role of such a beam stop changes. The locations (a through e) are continuous, not discrete, as long as the image and pupil, or conjugates thereof are excluded. As shown in FIG. 7, these locations may be both before and after the pupil.

Figure 8:
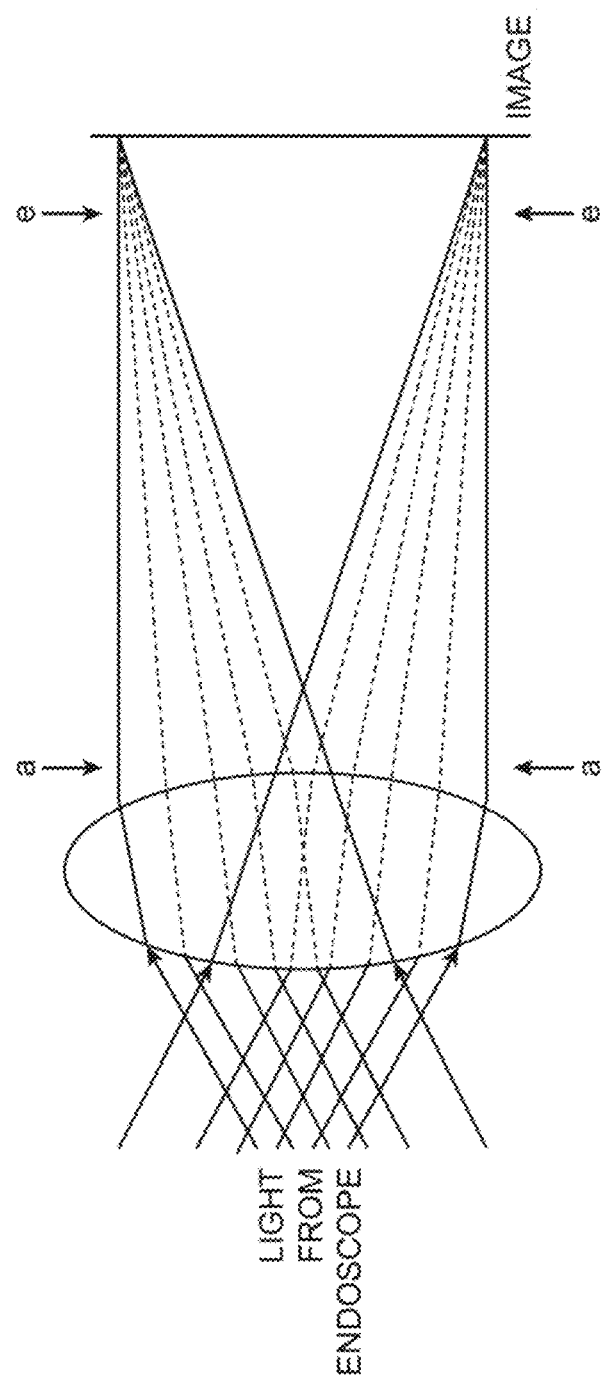
FIG. 8 illustrates a schematic view of axial locations for variable geometry vignetting after a pupil in an imaging system.

FIG. 8 illustrates axial locations for variable geometry wavelength dependent vignetting in an imaging system in which there is not a physical pupil or f-stop iris, i.e., the pupil or f-stop is in front of the imaging system, e.g., in some endoscope cameras (or "video couplers"). As such, vignetting may be introduced only after the pupil. Again, the locations are continuous, not discrete, as long as the image or conjugate thereof is excluded. Use of variable geometry wavelength dependent vignetting at this location may allow an aberrated beam output from an endoscope to be improved by a camera having variable geometry vignetting control.

Use of variable geometry wavelength dependent vignetting would enable off-axis performance to be improved. By way of example, suppose a camera is designed for use in a machine-vision application where the blue channel is of a shorter wavelength (460 nm for example) than the blue wavelength for which the endoscope was designed (F light, or 486 nm, for example). And further suppose that the off-axis image performance may be adversely affected by poor spot size on the blue channel since the operating wavelength is shorter than the design wavelength and the system exhibits lateral color. A camera that enables a user to stop down the blue light for the off-axis beam (vignette the blue) will show improved off-axis performance and the system will exhibit greater uniformity of performance across the field. After trimming the system's off-axis performance, a full-field white balancing is conducted after which the system is ready for use.

Figure 9:
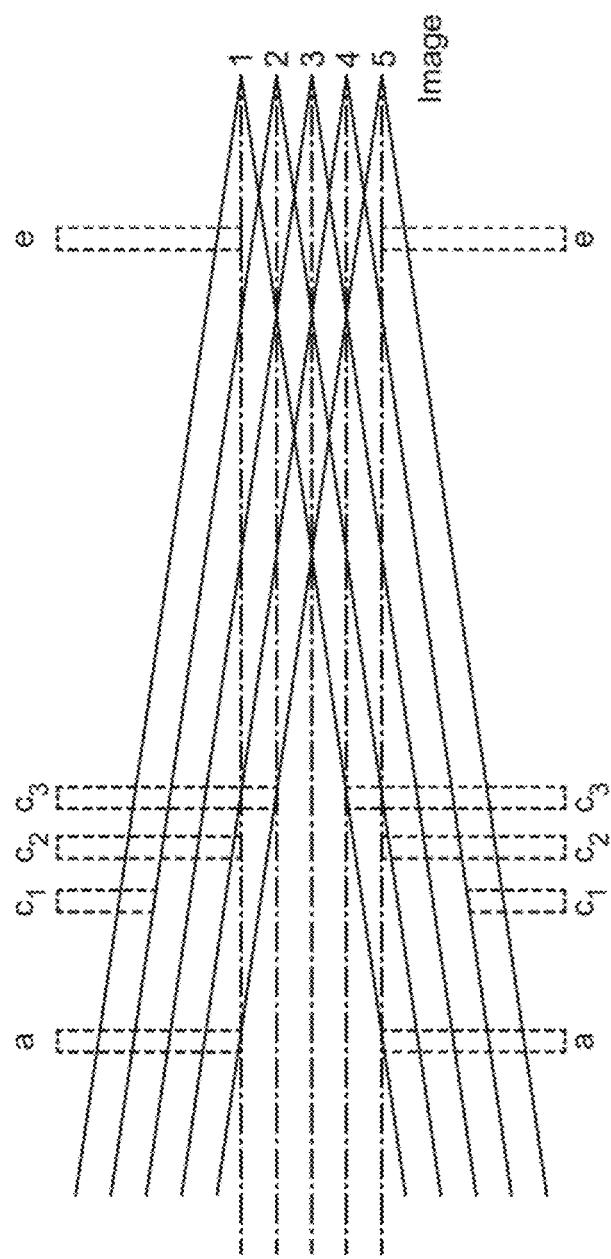
FIG. 9 illustrates a schematic view of axial locations for variable geometry vignetting according to an embodiment.

FIG. 9 illustrates additional cross-sectional details for variable geometry vignetting applied to an after stop (or "image space") beam. The vignetting may be introduce at any axial location a through e. Vignetting at positions closer to location "a" have wide transition regions (slow gradients in the image plane) since more image forming cones are affected for a given aperture size than is the case for apertures located closer to the image plane. In location "c" (indicated by c1, c2, c3) the variable is the aperture size itself. The insertion depth illustrated at location c3 applies vignetting to a larger portion of the field than does the insertion depth illustrated at location c1.

The variables associated with "variable geometry" are aperture size, aperture location, and the number of apertures. For example, an imaging system may have one variable aperture per wavelength range of interest. When positioned at the system aperture, the "aperture location" is no longer a variable. A variable geometry wavelength dependent aperture filter that transitions from the role of vignetting to the role of system aperture in a single architecture may be implemented.

Further to the example of variable geometry wavelength-dependent vignetting, a user may find the ideal field cut-off position (the limit of the vignetting function) by operating the aperture at a location nearer the image plane (locations nearer to e than a), then find a preferred transition region by moving away from the image plane. This process may be iterated and may be automated. Then, having found the desired setting, the camera is white balanced for the whole field. The system, e.g., an endoscope and a camera, are ready for use.

Figure 10:
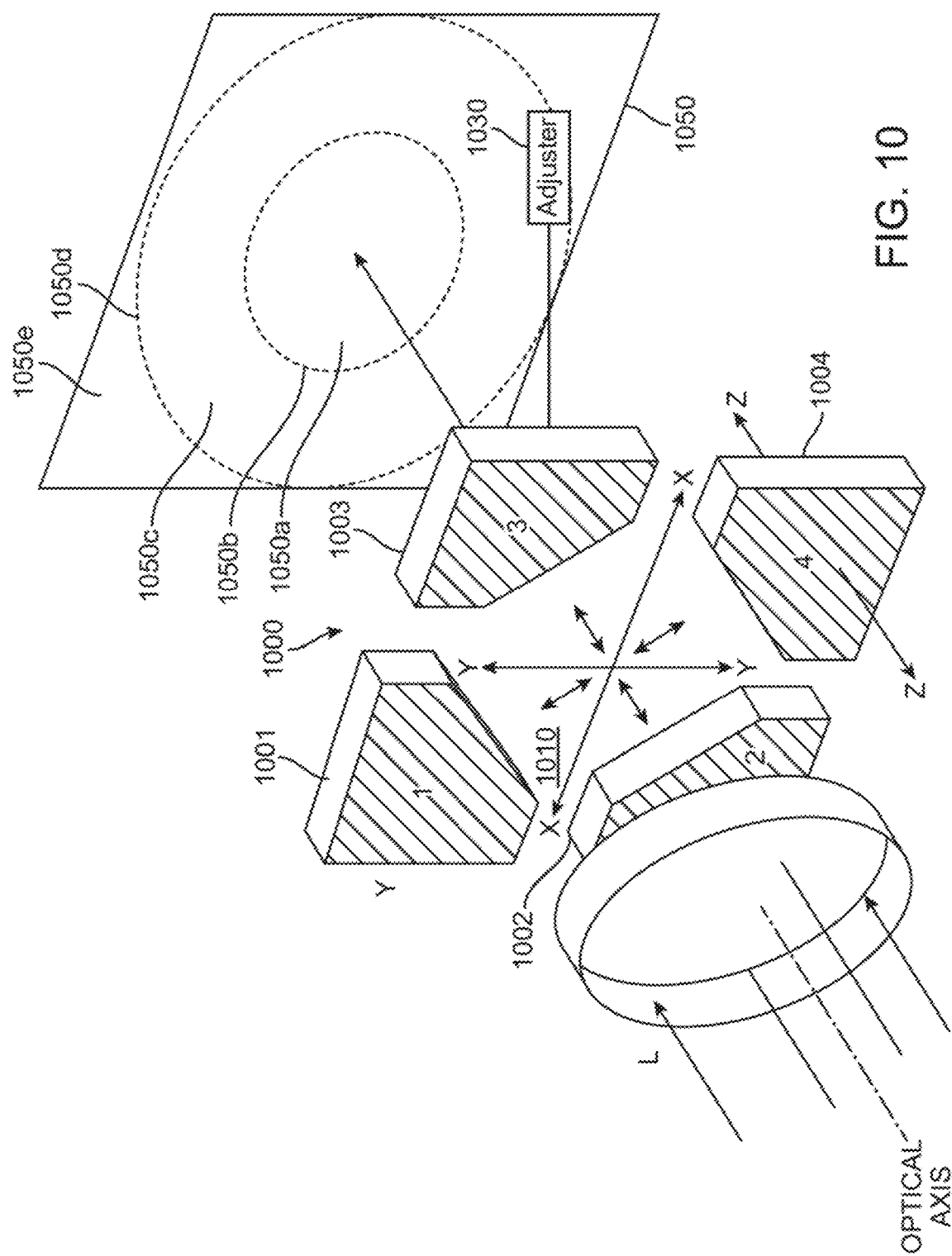
FIG. 10 illustrates a schematic view of variable geometry vignetting according to an embodiment.

FIG. 10 illustrates a filter 1000 in which four vanes or portions 1001-1004 are aligned to the rectilinear space of a downstream detector 1050 which is fully filled by an incident image. The vanes translate in the X-Y plane (to and from the optical axis) to adjust the aperture's size. The vanes translate axially parallel to Z (parallel to the optical axis) to adjust the aperture's location. The two adjustments together affect both the field position at which vignetting begins (indicated by the dashed line 1050b) the degree of vignetting that will occur, and the field position at which this degree is fully realized (indicated by dashed line 1050d). Such adjustment may be realized using an adjuster 1030, known to those of skill in the art, which may be operated manually or automated based on image quality. The region identified as 1050a is entirely unvignetted. The region identified as 1050e experiences the maximum degree of vignetting selected.

Figure 11:
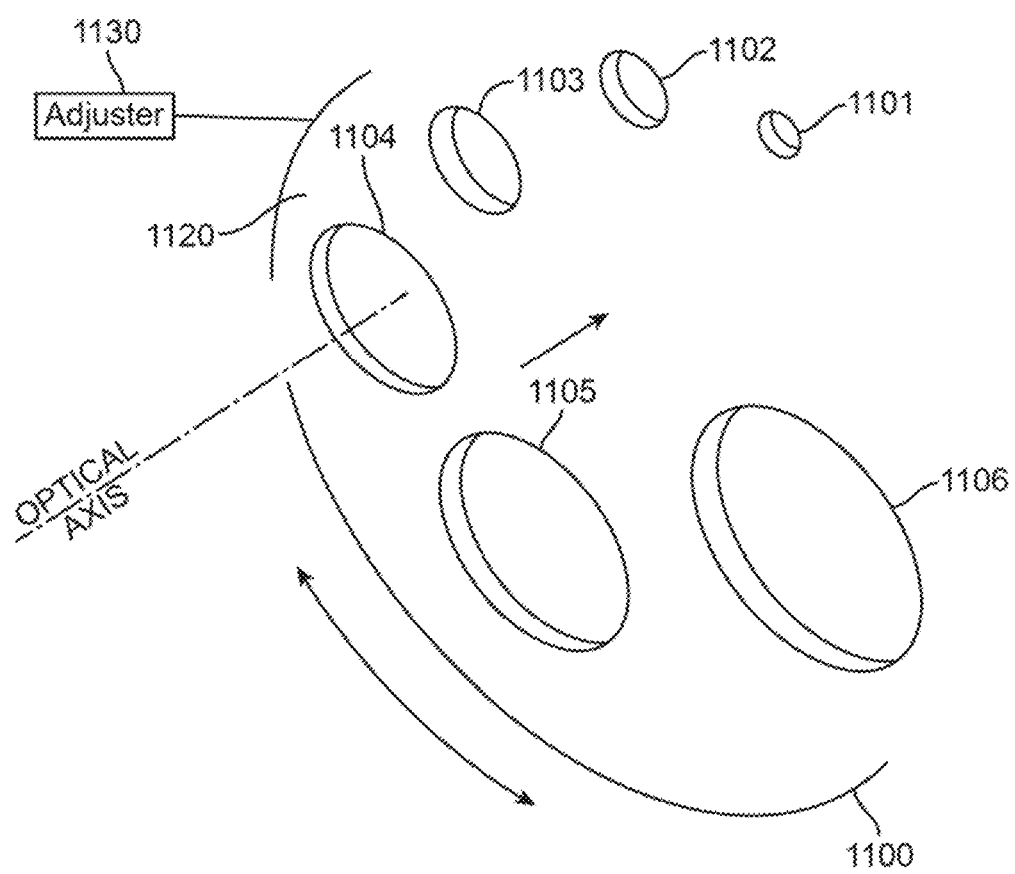
FIG. 11 illustrates a schematic view of variable geometry vignetting according to an embodiment.

FIG. 11 illustrates a filter 1100 in which a plurality of apertures 1101-1106 having different sizes are provided on a substrate 1120, e.g., a wheel, which is adjusted, e.g., rotated, by the adjuster 1130, either manually or automatically, to provide different aperture sizes. The substrate 1120 may be place at various positions along the optical axis.

APPLICATION #1

Multi-Channel Open-Field Fluorescence Imaging System

Figure 12A:
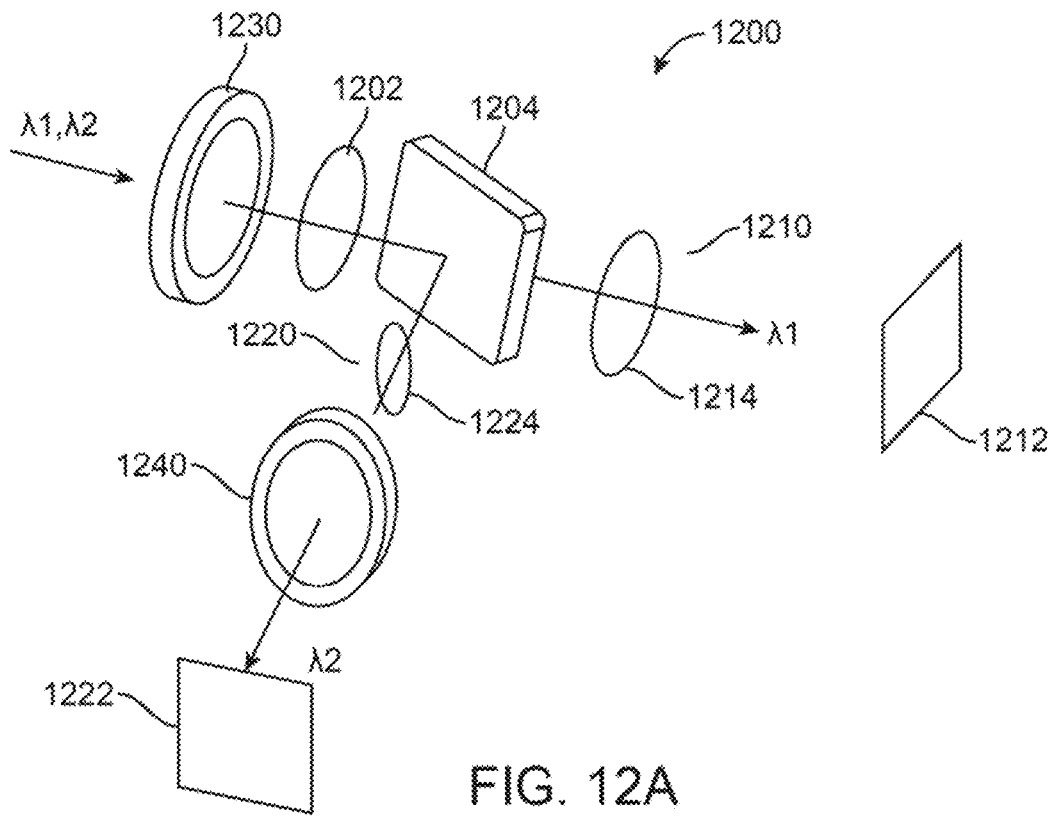
FIGS. 12A and 12B illustrate wavelength dependent vignetting in accordance with an embodiment having in a multi-channel visible and fluorescence imaging system.
Figure 12B:
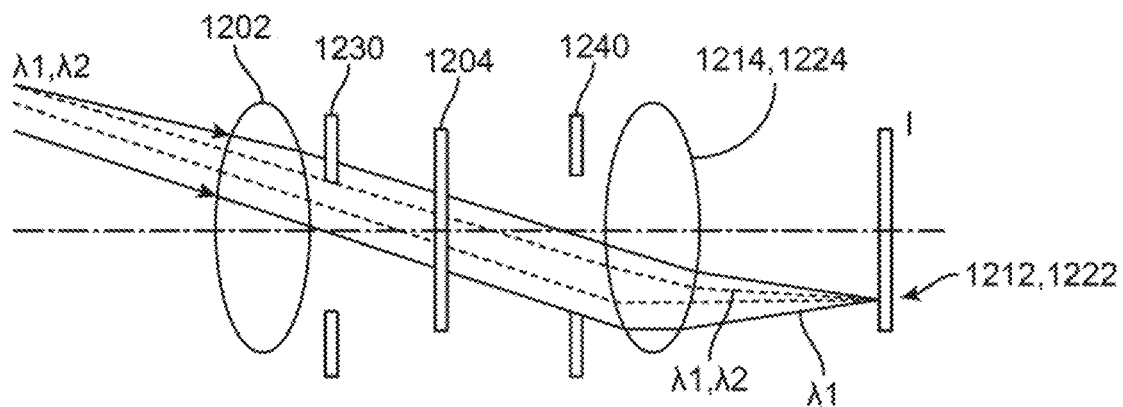

FIGS. 12A and 12B illustrate a schematic of a multi-channel open field fluorescence imaging system 1200. The system 1200 has two or more imaging channels 1210, 1220 have the same field of view and the same object field perspective. The system 1200 has image sensors 1212, 1222 having a common axis through an object field. The channels 1210, 1220 share a common objective lens 1202 and are separated somewhere between the objective lens 1202 and an image plane I, e.g., by a beamsplitter 1204. The system 1200 may also include a wavelength dependent filter aperture 1230 and an aperture 1240.

FIG. 12A illustrates two wavelength ranges entering the system. A first wavelength range λ1 includes a weak signal, e.g., a fluorescence signal, which can be orders of magnitude fainter than a second wavelength range λ2 that includes bright light, in this case visible light and the reflected portion of the laser excitation light. Both the visible light and the laser reflectance light are imaged for reasons related to other system requirements. Thus, the second wavelength range λ2 may include at least two non-adjacent wavelength sub-ranges or may have wavelength sub-ranges that partially overlap.

In the system 1200, weak intensity light λ1 (the fluorescence light) passes though at full aperture without limitation, apodization, obscuration, or vignetting. Thus, the first wavelength dependent filter aperture 1230 is transparent to the first wavelength range λ1, while both the wavelength dependent filter aperture 1230 and the aperture 1240 trim portions of the second wavelength range λ2.

As may be seen in FIG. 12B, the lower marginal rays in the off-axis beam of second wavelength range λ2 are stopped by the aperture 1240, which can be realized through traditional, non-wavelength dependent methods, as the first wavelength range λ1 has been split off and in not present in the channel 1220. In order to stop the upper marginal off-axis rays for second wavelength range λ2 the wavelength dependent filter aperture 1230 is used before the stop position. Since this wavelength dependent filter aperture 1230 also receives the first wavelength range λ1, the wavelength dependent filter aperture 1230 in accordance with embodiments set forth above may be used.

When the second wavelength range λ2 includes at least two wavelength sub-ranges, e.g., the bright visible and the very bright laser reflectance, additionally wavelength dependent vignetting may be realized even though these two wavelength sub-ranges share the same detector 1222. For example, the wavelength dependent filter aperture 1230 may have three regions, as illustrated in FIG. 5, and/or the aperture 1240 may be a wavelength dependent filter aperture in which more of the visible wavelength sub-range is transmitted than the laser reflectance wavelength sub-range, then the beam incident on the detector 1222 will require similar or identical camera electronics settings whether the laser reflectance or the visible light is to be imaged.

Thus, using a wavelength dependent filter aperture in accordance with embodiments in the system 1200 may allow fainter light to be collected and passed at the limit of what the optical design can manage, may improve off-axis performance of the brighter light, and, by allowing vignetting of the brighter light far upstream from the detector 1222, simplifies stray light control.

EXAMPLE APPLICATION #2

Two-Channel Laser Speckle Imaging System

Figure 13:
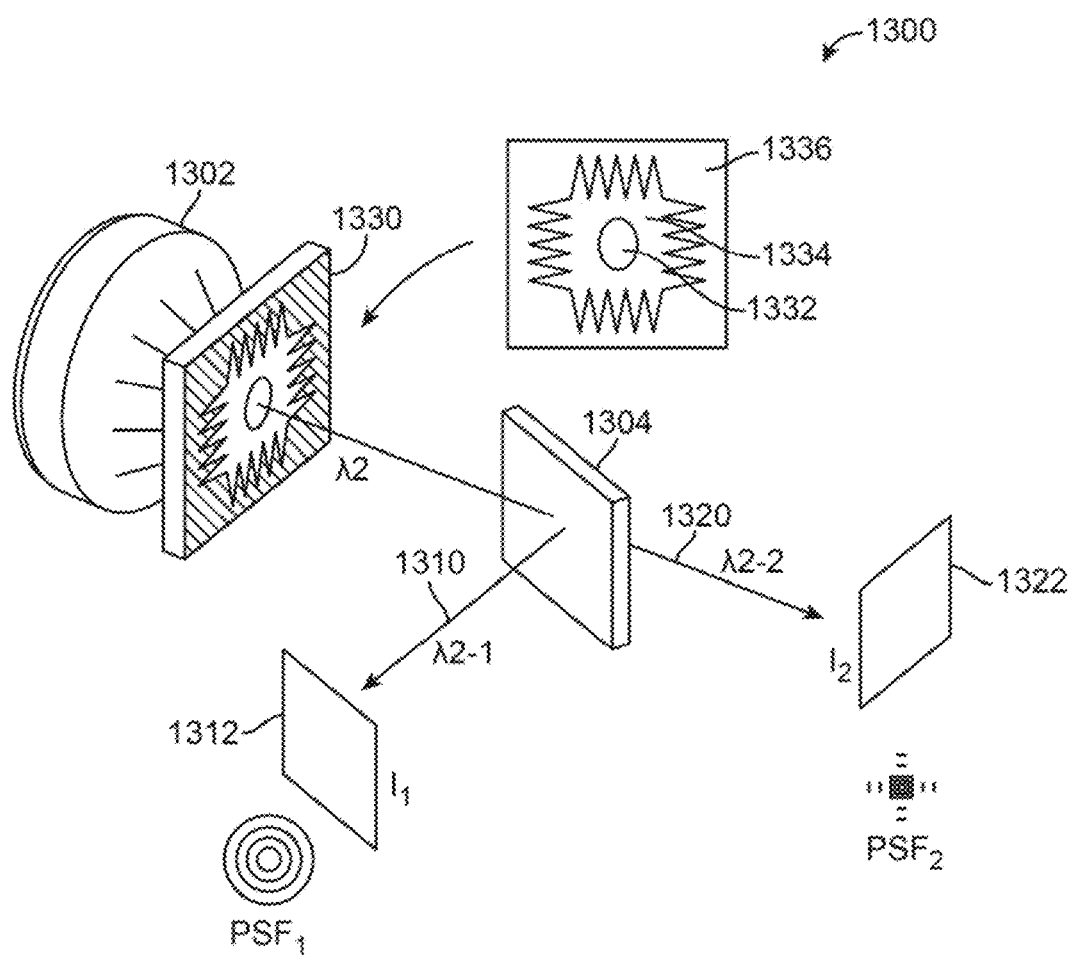
FIG. 13 illustrates wavelength dependent apodization in visible and laser speckle imaging system.

FIG. 13 illustrates a schematic form of a two-channel open field laser speckle imaging system 1300. The system 1300 includes at least two imaging channels 1310, 1320 that have the same field of view and object field perspective. The system may include a common objective lens 1302 and a wavelength dependent aperture filter 1330 located at the system aperture and it should be understood that other image forming optics exist after the aperture 1330 and may exist before and after the beam splitter 1304.

Similar to the system 1200, the system 1300 has sensors 1312, 1322 that have a common axis through the object field. For this reason, the channels share a common objective lens and are separated somewhere between the objective lens and the image plane, e.g., by a beamsplitter 1304, that splits the second wavelength range λ2 into a first wavelength sub-range λ2-1 of the visible light and a second wavelength sub-range λ2-2 of the reflected laser light.

In this example, the reflected laser light λ2-2 in the wavelength range λ2 is coherent and a speckle pattern or interference field is formed at the detector 1322. As shown in FIG. 13, the wavelength dependent aperture filter 1330 is positioned at the system aperture, or f-stop plane. The wavelength dependent aperture filter 1330 includes multiple band pass regions. In particular, a first or central region 1332, a second or transition region 1334, and a third or peripheral region 1336. The first region 1332 passes all light, but is bound by a circular annulus which defines the stop form, or system aperture for the visible light λ2-1. The visible light point spread function forms a traditional airy disk at detector 1312. The reflected laser light λ2-2 will also pass through the second region 1334 that includes a larger aperture bound by serrated edges along a square. Because the system aperture for the reflected laser light λ2-2 is larger than that for the visible light λ2-1, the reflected laser light λ2-2 forms a smaller point spread function at the detector 1322. Since the aperture is apodized with a feature designed to null much of the ringing outside the central core of the diffraction pattern, the point spread function at the detector 1322 produces less cross talk between speckle features and therefore higher contrast. In this example, the serrated aperture that bounds 1334 may be made to have a variable geometry, as this would enable control of speckle size incident upon the detector.

EXAMPLE APPLICATION #3

High-Resolution Visible & NIR Endoscope

Figure 14A:
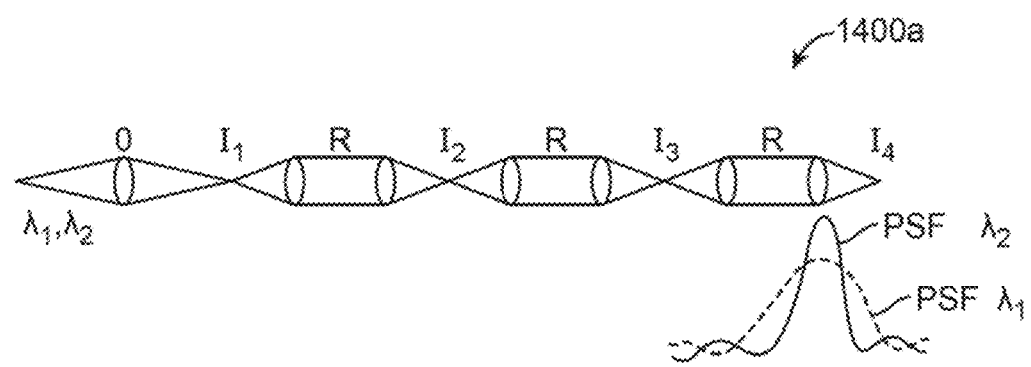
FIG. 14A illustrates an endoscope with multiple system aperture conjugate planes and point spread functions for two wavelengths.
Figure 14B:
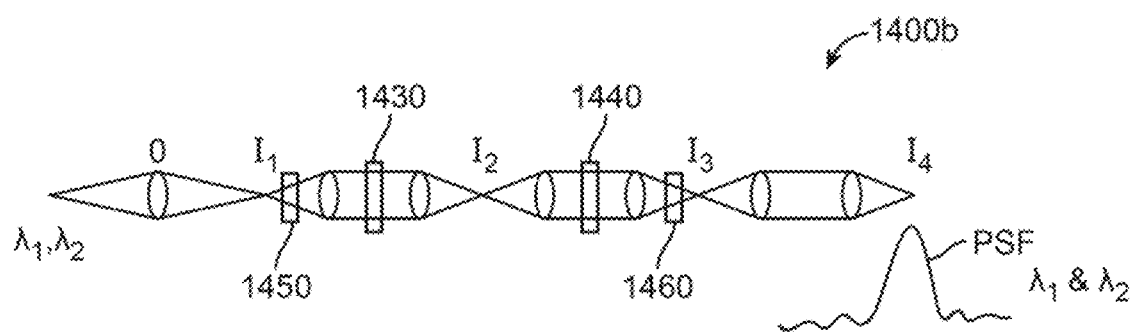
FIG. 14B illustrates an endoscope with multiple system aperture conjugate planes and point spread functions for two wavelengths.

FIGS. 14A and 14B respectively illustrate schematic views of a system 1400a without wavelength dependent filter apertures and a system 1400b with multiple wavelength dependent filter apertures 1430, 1440 at multiple system aperture conjugate planes and multiple wavelength dependent filter apertures 1450, 1460 at multiple vignetting planes. When a system, e.g., an endoscope, has an architecture that produces multiple conjugates of the system aperture and multiple conjugates of the image plane, then multiple wavelength dependent filter apertures may be employed. These may be used at system aperture conjugates in order to affect the point spread function for different wavelengths across the whole field. These also may be used at vignetting planes in order to affect the point spread function for different wavelengths throughout a portion of the off-axis field.

In a fluorescence endoscopic system, two competing interests impose constraints upon the same optical path: the weaker fluorescence signal is best managed without impedance or restriction on throughput, whereas the visible light image is pushed to ever-higher resolution as system architectures strive for larger and higher definition displays. Enhancements made to the visible light image quality should not result in lost throughput in the fluorescence signal.

Referring to the schematic in FIG. 14A, the point spread function for a portion of the visible light having wavelength range λ1 is broader than that of another portion of the visible light having wavelength range λ2. The difference in the point spreads may occur everywhere in the field, or it may occur in greater proportion for the off-axis field positions. The cause of the spread differential is not relevant, but by way of example, it may be inherent in the design, or it may be the result of an application that intends to use an existing design in a manner not originally intended (for example, using an existing, F, d, C-light optimized product in a machine vision application may introduce a broader spectral range than the endoscope can manage), or it may be that wavelength dependent apertures offer a more cost effective solution than can be realized through use of more lens elements. The reason for the difference in the point spread functions is not relevant. It is assumed here that an application wishes to reduce the difference between the PSF for a first set of wavelengths and the PSF for a second set of wavelengths (i.e. within the visible wavelengths) without impedance to a third set of wavelengths (i.e. the fluorescence wavelengths).

In FIG. 14B, the point spread functions of one or more wavelengths can be made to be more alike if they are altered through wavelength dependent apodization filters at the system aperture conjugates, and the point spread functions across the field of view can be made more alike if they are altered through wavelength dependent filters at vignetting planes. In particular, by placing wavelength dependent filter apertures 1430, 1440 in accordance with embodiments at the conjugate of the system aperture, the point spread function of the second wavelength range $\lambda 2$ may be equalized to that of the first wavelength range $\lambda 1$, without affecting a third wavelength range $\lambda 3$.

It should be appreciated that although FIGS. 14A and 14B only illustrate the optical path in the systems 1400a, 1400b, a full system includes a camera and, as such, another system aperture conjugate.

By way of summation and review, one or more embodiments may provide maximum or full-aperture throughput for the weaker signal, and an apodized wavelength dependent system aperture applied to a portion of the wavelengths of the stronger signal, may result in resolving finer line detail (higher contrast at the higher spatial frequencies) than would be the case for a system operating without an apodized wavelength dependent system aperture; and further enhancement may be realized in the off-axis performance through wavelength dependent vignetting. In particular, a filter may include a central filter region, the central filter region to transmit a first wavelength range, a peripheral filter region, the peripheral filter region to block a second wavelength range, and a transition filter region between the central and peripheral filter regions, the transition filter region to transmit or block the second wavelength range differently than the second wavelength range is to be transmitted or blocked in the central and peripheral filter regions. More generally, there may be "N" regions and up to N-1 transition regions, e.g., N-2 transition regions.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims. For example, while specific examples have been directed to endoscopes, embodiments may be used with other imaging system with similar wavelength ranges and single detector requirements, e.g., borescopes.

What is claimed is:

1. A system, comprising:
a filter including:
a central filter region, the central filter region to transmit a first wavelength range;
a peripheral filter region, the peripheral filter region to block a second wavelength range and to transmit the first wavelength range; and
a transition filter region between the central and peripheral filter regions, the transition filter region including a plurality of first portions and a plurality of second portions arranged in a pattern configured to apodize the boundary between the central and peripheral filter regions, said first portions for blocking the second wavelength range and said second portions for transmitting the second wavelength range, both the first and second portions transmitting the first wavelength range wherein the first wavelength range includes fluorescence light and the second wavelength range includes visible light, and the fluorescence light has a lower intensity compared to that of the visible light.

2. The system as claimed in claim 1, wherein the central filter region is to block the second wavelength range.

3. The system as claimed in claim 1, wherein the central filter region is to transmit the second wavelength range and the transition filter region is to transmit more of the second wavelength range than the peripheral filter region and less of the second wavelength range than the central filter region.

4. The system as claimed in claim 1, wherein the first portions of the transition filter region are of a same material as the peripheral filter region.

5. The system as claimed in claim 1, wherein the filter substantially equalizes point spread functions of the first and second wavelength ranges.

6. The system as claimed in claim 1, wherein the first and second wavelength ranges partially overlap.

7. The system as claimed in claim 1, wherein the first and second wavelength ranges do not overlap.

8. A kit, comprising:
a system as recited in claim 1; and
a beam splitter to split the first and second wavelength ranges.

9. The kit as claimed in claim 8, further comprising a plurality of relays.

10. The kit as claimed in claim 8, further comprising an objective lens.

11. An endoscope, comprising a system as recited in claim 1.

12. The endoscope as recited in claim 11, further comprising a second filter positioned at or near the system aperture or a conjugate thereof of the endoscope, wherein the second filter includes:
a second central filter region, the second central filter region to transmit the first wavelength range;
a second peripheral filter region, the second peripheral filter region to block the second wavelength range and to transmit the first wavelength range; and
a second transition filter region between the second central and second peripheral filter regions, the second transition filter region to transmit or block the second wavelength range differently than the second wavelength range is to be transmitted or blocked in the second central and second peripheral filter regions.

13. The endoscope as recited in claim 11, wherein the filter is spaced apart from the system aperture or conjugate thereof of the endoscope.

14. The system as claimed in claim 1, wherein the fluorescence light is an order of magnitude fainter than the visible light.

15. The system as claimed in claim 1, wherein the fluorescence light is infrared light.

16. The system as claimed in claim 1 wherein the filter is spaced apart from a system aperture of the system.

17. A system, comprising:
a filter including:
a central filter region, the central filter region to transmit a first wavelength range and a second wavelength range;

a peripheral filter region, the peripheral filter region to block the second wavelength range and to transmit the first wavelength range; and a transition filter region between the central and peripheral filter regions, the transition filter region to transmit more of the second wavelength range than the peripheral filter region and less of the second wavelength range than the central filter region, wherein the transition filter region includes a plurality of first portions and a plurality of second portions arranged in a pattern configured to apodize the boundary between the central and peripheral filter regions, said first portions that are to block the second wavelength range and second portions that are to transmit the second wavelength range, wherein both the first and second portions transmitting the first wavelength range; and the first wavelength range includes fluorescence light and the second wavelength range includes visible light, and the fluorescence light has a lower intensity compared to that of the visible light.

18. The system as claimed in claim 17, wherein the transition filter region increases blocking of the second wavelength range from the central filter region to the peripheral filter region.

19. The system as claimed in claim 17 wherein the filter is spaced apart from a system aperture of the system.

* * * * *